(12) United States Patent
Mitra et al.

(10) Patent No.: US 11,584,957 B2
(45) Date of Patent: *Feb. 21, 2023

(54) COLORIMETRIC DETECTION OF NUCLEIC ACID AMPLIFICATION

(71) Applicant: Lucira Health, Inc., Emeryville, CA (US)

(72) Inventors: Debkishore Mitra, Berkeley, CA (US); Ivan Krastev Dimov, Union City, CA (US); John Robert Waldeisen, Berkeley, CA (US)

(73) Assignee: Lucira Health, Inc., Emeryville, CA (US)

( * ) Notice: Subject to any disclaimer, the term of this patent is extended or adjusted under 35 U.S.C. 154(b) by 167 days.

This patent is subject to a terminal disclaimer.

(21) Appl. No.: 16/894,694

(22) Filed: Jun. 5, 2020

(65) Prior Publication Data

US 2020/0299758 A1    Sep. 24, 2020

Related U.S. Application Data

(63) Continuation of application No. 16/359,913, filed on Mar. 20, 2019, now Pat. No. 10,724,079, which is a continuation of application No. 15/306,240, filed as application No. PCT/US2015/027556 on Apr. 24, 2015, now Pat. No. 10,253,357.

(60) Provisional application No. 61/983,687, filed on Apr. 24, 2014.

(51) Int. Cl.
    *C12P 19/34*     (2006.01)
    *C12Q 1/6844*    (2018.01)

(52) U.S. Cl.
    CPC ......... *C12Q 1/6844* (2013.01); *C12Q 1/6846* (2013.01)

(58) Field of Classification Search
    CPC .......................... C12Q 1/6844; C12Q 1/6846
    See application file for complete search history.

(56) References Cited

U.S. PATENT DOCUMENTS

| | | |
|---|---|---|
| D244,555 S | 5/1977 | Wiedmann |
| 4,310,488 A | 1/1982 | Rahm et al. |
| 4,379,848 A | 4/1983 | Yeaw |
| 4,624,929 A | 11/1986 | Ullman |
| 4,849,340 A | 7/1989 | Oberhardt |
| 4,859,610 A | 8/1989 | Maggio |
| 4,936,682 A | 6/1990 | Hoyt |
| D334,065 S | 3/1993 | Collister |
| D371,605 S | 7/1996 | Wong et al. |
| 5,580,794 A | 12/1996 | Alien |
| 5,801,062 A | 9/1998 | Sarstedt et al. |
| 5,830,714 A | 11/1998 | Swaminathan et al. |
| 5,837,546 A | 11/1998 | Allen et al. |
| 5,888,826 A | 3/1999 | Ostgaard et al. |
| 5,958,349 A | 9/1999 | Petersen et al. |
| 6,071,394 A | 6/2000 | Cheng et al. |
| 6,074,606 A | 6/2000 | Sayles |
| 6,180,395 B1 | 1/2001 | Skiffington et al. |
| 6,198,107 B1 | 3/2001 | Seville |
| 6,300,142 B1 | 10/2001 | Andrewes et al. |
| 6,336,900 B1 | 1/2002 | Alleckson et al. |
| 6,352,838 B1 | 3/2002 | Krulevitch et al. |
| D456,082 S | 4/2002 | Bouse et al. |
| 6,564,968 B1 | 5/2003 | Terrell et al. |
| 6,565,808 B2 | 5/2003 | Hudak et al. |
| 6,699,384 B1 | 3/2004 | Lin et al. |
| 6,817,256 B2 | 11/2004 | Mehra et al. |
| 6,900,059 B1 | 5/2005 | Shinn et al. |
| D507,351 S | 7/2005 | Bimboim |
| 7,156,809 B2 | 1/2007 | Quy |
| 7,256,035 B1 | 8/2007 | Schnell et al. |
| D559,996 S | 1/2008 | Okamoto et al. |
| D560,812 S | 1/2008 | Powell et al. |
| D561,905 S | 2/2008 | Ramel et al. |
| D567,961 S | 4/2008 | Yajima |
| D574,507 S | 8/2008 | Muir et al. |

(Continued)

FOREIGN PATENT DOCUMENTS

| | | | |
|---|---|---|---|
| AU | 2003272465 A1 | 4/2004 | |
| CA | 2495252 A1 | 3/2004 | |

(Continued)

OTHER PUBLICATIONS

Anonymous: "Image Enhancement and Verification Tools—ABBYY Mobile Imaging SDK," Jul. 13, 2014, 12 pages.
Cao et al., "Microfluidic Chip for Molecular Amplication of Influenza A RNA in Human Respiratory Specimens," PLoS One, Mar. 2012, vol. 7, Issue 3, pp. 1-11.
European Search Report, International Application No. EP18780624, Dec. 4, 2020, 10 pages.
Extended European Search Report, European Published Application No. I 15557673 A1, May 25, 2021, 21 pages.
Foo et al., "Rapid Tests for the Diagnosis of Influenza," Australian Prescriber, vol. 32, No. 3, Jun. 2009, pp. 64-67.
Canadian Office Action for Application No. 2,944,994, dated Aug. 8, 2019, 3 pages.

(Continued)

*Primary Examiner* — Kenneth R Horlick
(74) *Attorney, Agent, or Firm* — Goodwin Procter LLP

(57) ABSTRACT

Colorimetry is used to detect amplification reaction products. A sample is contacted with a reaction mix under conditions such that an amplification reaction occurs and produces an amplification reaction product if the sample contains a target nucleic acid template molecule. The reaction mix includes an enzyme for catalyzing the amplification reaction, and at least one halochromic agent. If the target nucleic acid template molecule is present, the amplification reaction changes the starting pH of the reaction mix to cause a detectable colorimetric change of the halochromic agent, thereby indicating the presence of the target nucleic acid. If the target nucleic acid template molecule is not present, the amplification reaction does not generate an adequate number of protons to sufficiently change the starting pH of the reaction mix to cause a detectable colorimetric change of the halochromic agent, thereby indicating that the amplification reaction product has not been produced.

33 Claims, 16 Drawing Sheets

Specification includes a Sequence Listing.

(56) References Cited

U.S. PATENT DOCUMENTS

| | | |
|---|---|---|
| 7,438,852 B2 | 10/2008 | Tung et al. |
| 7,452,667 B2 | 11/2008 | Liew et al. |
| D602,599 S | 10/2009 | Xiaowei |
| D608,885 S | 1/2010 | Sneddon et al. |
| D618,351 S | 6/2010 | Hara |
| 7,850,922 B2 | 12/2010 | Gallagher et al. |
| D631,553 S | 1/2011 | Niedbala et al. |
| D659,848 S | 5/2012 | TerMaat et al. |
| D669,375 S | 10/2012 | Kao et al. |
| D675,335 S | 1/2013 | Feuerabend et al. |
| 8,372,353 B2 | 2/2013 | Lee et al. |
| D683,642 S | 6/2013 | Buesser et al. |
| D686,311 S | 7/2013 | Mori |
| D687,564 S | 8/2013 | Yang et al. |
| 8,719,989 B1 | 5/2014 | Qanaei |
| 9,034,606 B2 | 5/2015 | Tanner |
| 9,074,243 B2 | 7/2015 | Tanner |
| 9,074,249 B2 | 7/2015 | Tanner et al. |
| D736,403 S | 8/2015 | Hudson et al. |
| D743,571 S | 11/2015 | Jackson |
| D748,813 S | 2/2016 | Ishiguro et al. |
| D749,420 S | 2/2016 | Maggio |
| 9,278,321 B2 | 3/2016 | Dale et al. |
| D773,069 S | 11/2016 | Curry |
| 9,546,358 B2 | 1/2017 | Tanner et al. |
| D787,682 S | 5/2017 | Ockham et al. |
| D791,952 S | 7/2017 | Florescu et al. |
| 9,739,743 B2 | 8/2017 | Athanasiou et al. |
| D800,912 S | 10/2017 | Uzri et al. |
| 9,815,061 B2 | 11/2017 | Delattre et al. |
| D808,833 S | 1/2018 | Abbott et al. |
| D820,130 S | 6/2018 | Khattak et al. |
| D821,602 S | 6/2018 | Sever et al. |
| 9,999,889 B2 | 6/2018 | Khattak et al. |
| D825,772 S | 8/2018 | Sever et al. |
| D829,336 S | 9/2018 | Wohlstadter et al. |
| D829,337 S | 9/2018 | Klein et al. |
| 10,093,965 B2 | 10/2018 | Toumazou et al. |
| 10,146,909 B2 | 12/2018 | Dimov et al. |
| D838,379 S | 1/2019 | Trump |
| D840,049 S | 2/2019 | Schulz et al. |
| 10,195,606 B2 | 2/2019 | Khattak et al. |
| 10,253,357 B2 | 4/2019 | Mitra et al. |
| 10,272,434 B2 | 4/2019 | Khattak et al. |
| D854,703 S | 7/2019 | Juhlin et al. |
| D855,212 S | 7/2019 | Komuro |
| 10,343,160 B2 | 7/2019 | Lemoine et al. |
| D859,683 S | 9/2019 | Harding et al. |
| D860,472 S | 9/2019 | Blake et al. |
| D865,212 S | 10/2019 | Kakuda et al. |
| D865,218 S | 10/2019 | Mathers et al. |
| 10,449,538 B1 | 10/2019 | Carrano et al. |
| D867,584 S | 11/2019 | Zercher et al. |
| D869,311 S | 12/2019 | Khattak et al. |
| 10,545,161 B2 | 1/2020 | Khattak et al. |
| D874,677 S | 2/2020 | Stamm et al. |
| D875,963 S | 2/2020 | Gruen |
| 10,549,275 B2 | 2/2020 | Myers, III et al. |
| D879,319 S | 3/2020 | Kakuda et al. |
| D879,320 S | 3/2020 | Kakuda et al. |
| D879,994 S | 3/2020 | Leimkuehler et al. |
| 10,589,267 B2 | 3/2020 | Khattak et al. |
| 10,603,664 B2 | 3/2020 | Khattak et al. |
| D882,110 S | 4/2020 | Klein et al. |
| D883,515 S | 5/2020 | Jenoski et al. |
| D886,901 S | 6/2020 | Hussey et al. |
| 10,843,185 B2 | 11/2020 | Gorin et al. |
| D907,232 S | 1/2021 | Reber et al. |
| D923,797 S | 6/2021 | Parks et al. |
| D928,341 S | 8/2021 | Thimm et al. |
| 2001/0012612 A1 | 8/2001 | Petersen et al. |
| 2002/0001539 A1 | 1/2002 | DiCesare et al. |
| 2002/0039783 A1 | 4/2002 | McMillan et al. |
| 2002/0042125 A1 | 4/2002 | Petersen et al. |
| 2003/0064526 A1 | 4/2003 | Niedbala et al. |
| 2003/0082632 A1 | 5/2003 | Shumate |
| 2003/0123994 A1 | 7/2003 | Weng et al. |
| 2003/0157503 A1 | 8/2003 | McGarry et al. |
| 2004/0018634 A1 | 1/2004 | Hajizadeh et al. |
| 2004/0052689 A1 | 3/2004 | Yao |
| 2004/0118189 A1 | 6/2004 | Karp et al. |
| 2004/0166569 A1 | 8/2004 | Marziali et al. |
| 2004/0203174 A1 | 10/2004 | Jones et al. |
| 2004/0208792 A1 | 10/2004 | Linton et al. |
| 2004/0209275 A1 | 10/2004 | Liew et al. |
| 2005/0022895 A1 | 2/2005 | Barth et al. |
| 2005/0221281 A1 | 10/2005 | Ho |
| 2006/0078929 A1 | 4/2006 | Bickel et al. |
| 2006/0094004 A1 | 5/2006 | Nakajima et al. |
| 2006/0166354 A1 | 7/2006 | Wikswo et al. |
| 2006/0194207 A1 | 8/2006 | Mitani et al. |
| 2006/0245977 A1 | 11/2006 | Bodner |
| 2007/0014695 A1 | 1/2007 | Yue et al. |
| 2007/0166200 A1 | 7/2007 | Zhou et al. |
| 2007/0183934 A1 | 8/2007 | Diercks et al. |
| 2007/0217963 A1 | 9/2007 | Elizarov et al. |
| 2008/0000892 A1 | 1/2008 | Hirano et al. |
| 2008/0038713 A1 | 2/2008 | Gao et al. |
| 2008/0056948 A1 | 3/2008 | Dale et al. |
| 2008/0149840 A1 | 6/2008 | Handique et al. |
| 2008/0204380 A1 | 8/2008 | Shin et al. |
| 2008/0233015 A1 | 9/2008 | Turner |
| 2009/0004732 A1 | 1/2009 | LaBarre et al. |
| 2009/0048115 A1 | 2/2009 | Liew et al. |
| 2009/0071911 A1 | 3/2009 | Folden et al. |
| 2009/0151864 A1 | 6/2009 | Burke et al. |
| 2009/0203973 A1 | 8/2009 | Donoghue et al. |
| 2009/0305315 A1 | 12/2009 | Gandola et al. |
| 2009/0308185 A1 | 12/2009 | Wu et al. |
| 2009/0320684 A1 | 12/2009 | Weaver et al. |
| 2010/0015611 A1 | 1/2010 | Webster et al. |
| 2010/0229956 A1 | 9/2010 | Luyendijk |
| 2010/0323919 A1 | 12/2010 | Chen et al. |
| 2010/0331219 A1 | 12/2010 | Munenaka |
| 2011/0003330 A1 | 1/2011 | Durack |
| 2011/0005932 A1 | 1/2011 | Jovanovich et al. |
| 2011/0124098 A1 | 5/2011 | Rose et al. |
| 2011/0151432 A1 | 6/2011 | Zappia et al. |
| 2011/0172510 A1 | 7/2011 | Chickering, III et al. |
| 2011/0294112 A1 | 12/2011 | Bearinger et al. |
| 2011/0294205 A1 | 12/2011 | Hukari et al. |
| 2012/0040445 A1 | 2/2012 | Bouma et al. |
| 2012/0100624 A1 | 4/2012 | Hara et al. |
| 2012/0105837 A1 | 5/2012 | Ingber |
| 2012/0285562 A1 | 11/2012 | Richardson |
| 2013/0003162 A1 | 1/2013 | Leoni et al. |
| 2013/0112296 A1 | 5/2013 | Lee et al. |
| 2013/0130232 A1 | 5/2013 | Weibel et al. |
| 2013/0244241 A1 | 9/2013 | Carrera et al. |
| 2013/0266948 A1 | 10/2013 | Bird et al. |
| 2013/0280725 A1 | 10/2013 | Ismagilov et al. |
| 2013/0295663 A1 | 11/2013 | Weight et al. |
| 2013/0323738 A1 | 12/2013 | Tanner et al. |
| 2013/0323793 A1 | 12/2013 | Tanner et al. |
| 2014/0031248 A1 | 1/2014 | Tanner et al. |
| 2014/0057210 A1 | 2/2014 | Malik et al. |
| 2014/0057268 A1 | 2/2014 | Tanner et al. |
| 2014/0073013 A1 | 3/2014 | Gorman et al. |
| 2014/0073043 A1 | 3/2014 | Holmes |
| 2014/0170661 A1 | 6/2014 | Lamura et al. |
| 2014/0188089 A1 | 7/2014 | Midgette et al. |
| 2014/0228773 A1 | 8/2014 | Burkholz |
| 2014/0242612 A1 | 8/2014 | Wang et al. |
| 2014/0335505 A1 | 11/2014 | Holmes |
| 2014/0356874 A1 | 12/2014 | Bearinger |
| 2015/0024436 A1 | 1/2015 | Eberhart et al. |
| 2015/0111201 A1 | 4/2015 | Ozcan et al. |
| 2015/0132795 A1 | 5/2015 | Griswold et al. |
| 2015/0151300 A1 | 6/2015 | Williams et al. |
| 2015/0154449 A1 | 6/2015 | Ito et al. |
| 2015/0182966 A1 | 7/2015 | Coursey |
| 2015/0240293 A1 | 8/2015 | Tanner et al. |
| 2015/0247190 A1 | 9/2015 | Ismagilov et al. |
| 2015/0298118 A1 | 10/2015 | Chard et al. |

(56) References Cited

U.S. PATENT DOCUMENTS

| | | |
|---|---|---|
| 2015/0321193 A1 | 11/2015 | Sprague et al. |
| 2015/0328638 A1 | 11/2015 | Handique et al. |
| 2015/0359458 A1 | 12/2015 | Erickson et al. |
| 2016/0077015 A1 | 3/2016 | Holmes et al. |
| 2016/0194685 A1 | 7/2016 | Unger et al. |
| 2016/0216287 A1 | 7/2016 | Holmes et al. |
| 2016/0275149 A1 | 9/2016 | Majumdar et al. |
| 2016/0288121 A1 | 10/2016 | Ismagilov et al. |
| 2016/0334403 A1 | 11/2016 | Gibbons et al. |
| 2017/0044599 A1 | 2/2017 | Mitra et al. |
| 2018/0293350 A1 | 10/2018 | Dimov et al. |
| 2018/0372595 A1 | 12/2018 | Pais et al. |
| 2019/0050988 A1 | 2/2019 | Dimov et al. |
| 2019/0060895 A1 | 2/2019 | Myers, III et al. |
| 2019/0076841 A1 | 3/2019 | Myers, III et al. |
| 2019/0083975 A1 | 3/2019 | Mitra et al. |
| 2019/0094114 A1 | 3/2019 | Myers, III et al. |
| 2019/0309356 A1 | 10/2019 | Mitra et al. |
| 2019/0314810 A1 | 10/2019 | Khattak et al. |
| 2020/0030798 A1 | 1/2020 | Mitra et al. |
| 2020/0122142 A1 | 4/2020 | Myers, III et al. |
| 2020/0164373 A1 | 5/2020 | Khattak et al. |
| 2020/0290035 A1 | 9/2020 | Samsoondar |
| 2020/0323474 A1 | 10/2020 | McIntosh |
| 2021/0378643 A1 | 12/2021 | Roswech et al. |

FOREIGN PATENT DOCUMENTS

| | | |
|---|---|---|
| CN | 101821619 A | 9/2010 |
| CN | 104937108 A | 9/2015 |
| CN | 105441312 A | 3/2016 |
| CN | 201930535293.7 | 4/2020 |
| EP | 0056241 A1 | 7/1981 |
| EP | 0520408 A2 | 12/1992 |
| EP | 1557673 A1 | 7/2005 |
| EP | 1661988 A1 | 5/2006 |
| EP | 2251435 A1 | 11/2010 |
| IN | 287440 | 8/2019 |
| JP | 62-151198 A | 7/1987 |
| JP | 2008-173218 A | 7/2008 |
| JP | 2010-061383 A | 3/2010 |
| JP | 2010-538801 A | 12/2010 |
| JP | 2013-526867 A | 6/2013 |
| JP | 2013-532488 A | 8/2013 |
| JP | 2013-228350 A | 11/2013 |
| JP | 2016-522676 A | 8/2016 |
| JP | 2017-513531 A | 6/2017 |
| WO | 1997/011723 A1 | 4/1997 |
| WO | 9712681 A1 | 4/1997 |
| WO | 1997/041421 A1 | 11/1997 |
| WO | 2004/024892 A2 | 3/2004 |
| WO | 2005/012518 A1 | 2/2005 |
| WO | 2008/060604 A2 | 5/2008 |
| WO | 2008/107014 A1 | 9/2008 |
| WO | 2009/033178 A1 | 3/2009 |
| WO | 2009/039259 A1 | 3/2009 |
| WO | 2009/125227 A1 | 10/2009 |
| WO | 2010/091080 A2 | 8/2010 |
| WO | 2010/119377 A1 | 10/2010 |
| WO | 2010/132453 A2 | 11/2010 |
| WO | 2011/110873 A1 | 9/2011 |
| WO | 2011/123064 A1 | 10/2011 |
| WO | 2011/144345 A1 | 11/2011 |
| WO | 2012/018741 A2 | 2/2012 |
| WO | 2012/045889 A1 | 4/2012 |
| WO | 2013/008042 A1 | 1/2013 |
| WO | 2013/080154 A1 | 6/2013 |
| WO | 2014/018828 A1 | 1/2014 |
| WO | 2014/019829 A1 | 2/2014 |
| WO | 2014/020326 A2 | 2/2014 |
| WO | 2014/031783 A1 | 2/2014 |
| WO | 2015/037281 A1 | 5/2014 |
| WO | 2014/144548 A2 | 9/2014 |
| WO | 2015164770 A1 | 10/2015 |
| WO | 2015/184360 A1 | 12/2015 |
| WO | 2017/160836 A1 | 9/2017 |
| WO | 2017/160838 A1 | 9/2017 |
| WO | 2017/160839 A1 | 9/2017 |
| WO | 2017/160840 A1 | 9/2017 |
| WO | 2018/140540 A1 | 8/2018 |
| WO | 2018185573 A1 | 10/2018 |
| WO | 2019/055135 A1 | 3/2019 |
| WO | 2020/180858 A1 | 9/2020 |

OTHER PUBLICATIONS

European Application No. 17767336.5, Extended European Search Report dated Sep. 26, 2019, 14 pages.
European Application No. 17767337.3, Extended European Search Report dated Sep. 18, 2019, 6 pages.
European Application No. 17767339.9, Extended European Search Report dated Oct. 4, 2019, 11 pages.
European Search Report for European Patent Application No. EP 19178796.9, dated Oct. 9, 2019, 7 Pages.
Goto., M., et al., "Colorimetric detection of loop-mediated isothermal amplification reaction by using hydroxy naphthol blue", BIOTECHNIQUES, Mar. 1, 2009, pp. 167-172, vol. 46, No. 3.
Non-Final Office Action for United States U.S. Appl. No. 15/306,240, dated Jul. 24, 2018, 8 pages.
Non-Final Office Action for United States U.S. Appl. No. 16/359,913, dated Oct. 1, 2019, 9 pages.
Non-Final Office Action for United States U.S. Appl. No. 29/674,581, dated Jan. 8, 2020, 11 pages.
Partial Supplemental European Search Report for European Patent Application No. EP 17767338.1, dated Oct. 10, 2019, 15 Pages.
Patent Cooperation Treaty, International Search Report and Written Opinion of the International Searching Authority, International Patent Application No. PCT/US19/55365, dated Feb. 5, 2020, 20 Pages.
Patent Cooperation Treaty, International Search Report and Written Opinion of the International Searching Authority, International Patent Application No. PCT/US2015/027556, dated Sep. 15, 2015, 18 Pages.
Patent Cooperation Treaty, International Search Report and Written Opinion of the international Searching Authority, International Patent Appiication No. PCT/US2017/022300, dated Jul. 10, 2017, 15 Pages.
Patent Cooperation Treaty, International Search Report and Written Opinion of the International Searching Authority, International Patent Appiication No. PCT/US2017/022304, dated Jul. 25, 2017, 20 Pages.
Patent Cooperation Treaty, International Search Report and Written Opinion of the International Searching Authority, International Patent Application No. PCT/US2017/022305, dated Jul. 19, 2017, 20 Pages.
Patent Cooperation Treaty, International Search Report and Written Opinion of the International Searching Authority, International Patent Application No. PCT/US2017/022306, dated Jun. 5, 2017, 18 Pages.
PCT International Search Report and Written Opinion for PCT/IB2018/051326, dated Jun. 26, 2018, 15 pages.
PCT International Search Report and Written Opinion for PCT/US2018/044044, dated Sep. 26, 2018, 13 Pages.
Supplementary European Search Report for European Patent Application No. EP 15783787, dated Nov. 28, 2017, 8 Pages.
Supplementary European Search Report for European Patent Application No. EP 17767338.1, dated Jan. 10, 2020, 13 Pages.
Westcott, S.L., et al., "Broadband optical absorbance spectroscopy using a whispering gallery mode microsphere resonator," Review of Scientific Instruments, vol. 79, No. 3, Mar. 13, 2008, 9 Pages.
FDA Approves in-home, rapid results COVID-19 test. Online, published Nov. 18, 2020.
Notification of Transmittal of the International Search Report and the Written Opinion of the International Searching Authority, or the Declaration, Int'l Application No. PCT/US20/20772, Jun. 10, 2020, 15 pages.

(56) References Cited

OTHER PUBLICATIONS

Notification of Transmittal of the International Search Report and the Written Opinion of the International Searching Authority, of the Declaration, Int'l Application No. PCT/2021/049178, dated Jan. 14, 2022, 20 pages.

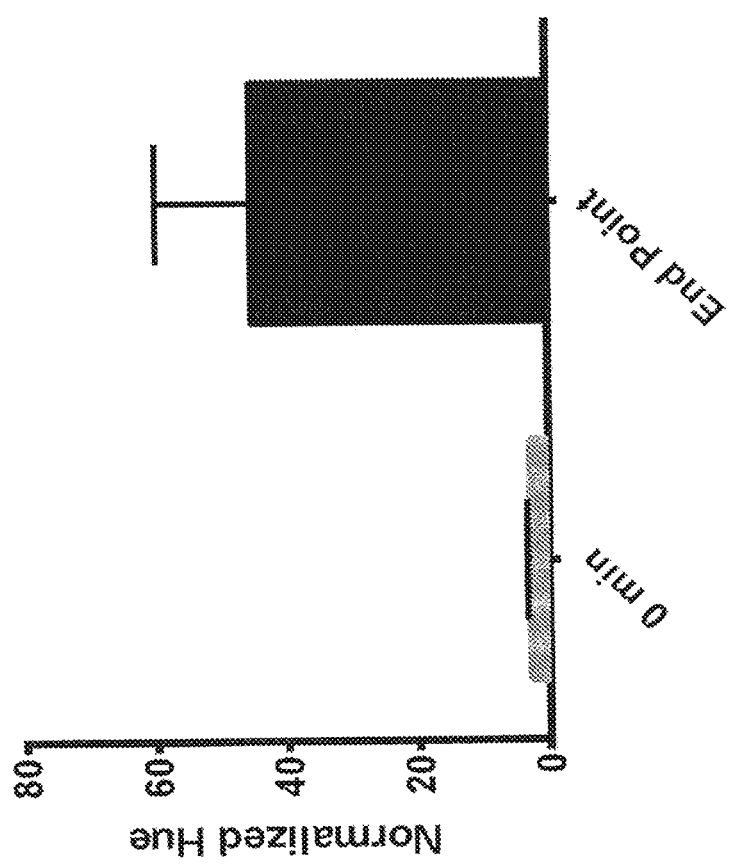

COLORIMETRIC DETECTION OF NUCLEIC ACID AMPLIFICATION

CROSS REFERENCE TO RELATED APPLICATIONS

This application is a continuation of U.S. patent application Ser. No. 16/359,913, issued as U.S. Pat. No. 10,724,079, filed Mar. 20, 2019, which is a continuation of U.S. patent application Ser. No. 15/306,240, issued as U.S. Pat. No. 10,253,357, filed Oct. 24, 2016, which is the national stage of International (PCT) Patent Application Serial No. PCT/US2015/027556, filed Apr. 24, 2015, which claims the benefit of U.S. provisional application 61/983,687, filed Apr. 24, 2014, the contents of which are hereby incorporated by reference in their entirety.

STATEMENT REGARDING FEDERALLY SPONSORED RESEARCH OR DEVELOPMENT

This invention was made with government support under Grant No. 1R43OD016718-01A1 awarded by the Small Business Innovation Research Program at the National Institutes of Health. The government has certain rights in the invention.

SEQUENCE LISTING

The instant application contains a Sequence Listing which has been filed electronically in ASCII format and is hereby incorporated by reference in its entirety. Said ASCII copy, created on Jun. 5, 2020, is named DSS-001C2_CRF_sequencelisting.txt and is 5,646 bytes in size.

BACKGROUND OF THE INVENTION

Field of the Invention

The invention relates to methods and compositions for colorimetric detection of nucleic acid amplification reaction products. In particular, the invention relates to accelerated colorimetric detection of nucleic acid amplification reaction products, using a reaction mix including one or more halochromic agents.

Description of the Related Art

Some current methods for the detection of specific nucleic acid sequences and nucleic acid biomarkers involve fluorescence methods. DNA primers are designed to amplify nucleic acid sequences from a sample using nucleic acid amplification schemes such as PCR (polymerase chain reaction) and LAMP (loop-mediated amplification). Typically, the resulting amplicons are detected and quantified through fluorescence techniques using an intercalating fluorophore or molecular probe. However, these techniques require sophisticated instrumentation, including optical components, an excitation source, and one or more sensors for detection of the fluorescent emission. These instruments are potentially large, cumbersome, and expensive. Alternatively, the amplicons can be colorimetrically visualized using agarose gels or lateral flow assays. However, these techniques require additional steps, which increase the time to result, and in some cases need instrumentation such as a gel box.

SUMMARY OF THE INVENTION

Disclosed herein are methods and kits for colorimetric detection of an amplification reaction product. The methods include contacting the sample with a reaction mix under conditions such that an amplification reaction occurs and produces an amplification reaction product if the sample contains a target nucleic acid template molecule. The reaction mix includes an enzyme for catalyzing the amplification reaction, and a halochromic agent. In some embodiments, the reaction mix includes more than one halochromic agent. In some embodiments, the reaction mix also includes a buffer having a buffering capacity equivalent to Tris buffer at a concentration between 1 mM-19 mM in a solution having a starting pH of 8.0. If the target nucleic acid template molecule is present, the amplification reaction changes the starting pH of the reaction mix to cause a detectable colorimetric change of the halochromic agent, thereby indicating the presence of the target nucleic acid. In some embodiments, the detectable colorimetric change is quantified at a cell path length of 50 μm. If the target nucleic acid template molecule is not present, the amplification reaction does not generate an adequate number of protons to sufficiently change the starting pH of the reaction mix to cause a detectable colorimetric change of the halochromic agent, thereby indicating that the amplification reaction product has not been produced.

The kit includes an enzyme for catalyzing an amplification reaction, a halochromic agent, and optionally a buffer having a buffering capacity equivalent to Tris buffer at a concentration between 1 mM-19 mM in a solution having a starting pH of 8.0. The kit further includes instructions for use comprising instructions for contacting a sample with a reaction mix including the buffer and the enzyme and the halochromic agent under conditions that an amplification reaction occurs and produces an amplification reaction product if the sample contains a target nucleic acid template molecule, the reaction mix having a starting pH. If the target nucleic acid template molecule is present, the amplification reaction changes the starting pH of the reaction mix to cause a detectable colorimetric change of the halochromic agent, thereby indicating the presence of the target nucleic acid. If the target nucleic acid template molecule is not present, the amplification reaction does not generate an adequate number of protons to sufficiently change the starting pH of the reaction mix to cause a detectable colorimetric change of the halochromic agent, thereby indicating that the amplification reaction product has not been produced.

BRIEF DESCRIPTION OF THE SEVERAL VIEWS OF THE DRAWINGS

These and other features, aspects, and advantages of the present invention will become better understood with regard to the following description, and accompanying drawings, where:

FIGS. 7A, 7B, 7C, and 7D show the normalized hue values for amplification reactions using various halochromic agent concentrations, according to an embodiment.

DETAILED DESCRIPTION OF THE INVENTION

Figure 1:
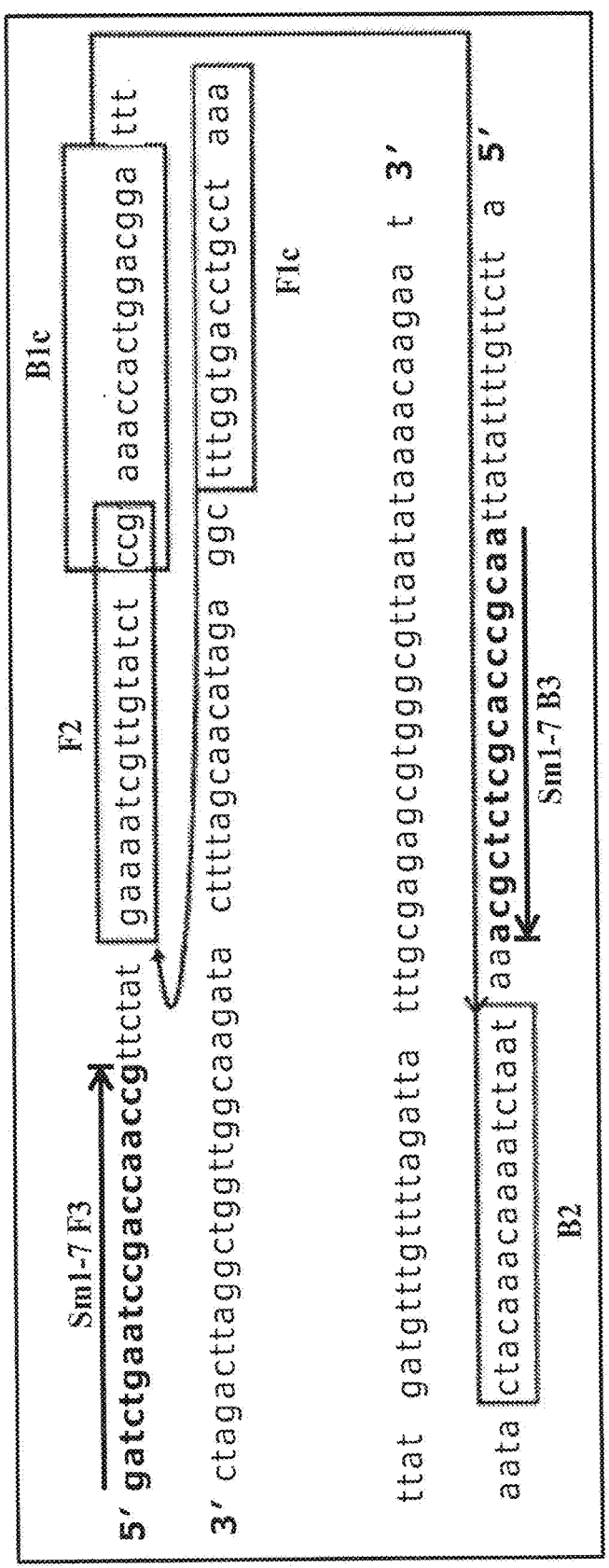
FIG. 1 shows the DNA sequence of a template nucleic acid molecule target region from *Schistosoma mansoni* (SEQ ID NO: 23), according to an embodiment.

Disclosed herein are compositions and methods for colorimetric detection of nucleic acid amplification reaction products. In some embodiments, amplified reaction products are detected by a visual color change observation or by measuring absorbance or fluorescence of the color change of a halochromic agent in the amplification reaction mix.

Definitions

Terms used in the claims and specification are defined as set forth below unless otherwise specified.

The term "colorimetry" or "colorimetric" refers to techniques of quantifying or otherwise observing colored compound concentrations in solution. "Colorimetric detection" refers to any method of detecting such colored compounds and/or the change in color of the compounds in solution. Methods may include visual observation, absorbance measurements, or fluorescence measurements, among others.

The term "halochromic agent" refers to a composition that changes color upon some chemical reaction. In particular, a halochromic agent can refer to a composition that changes color with a pH change. Different halochromic agents may change colors over different pH transition ranges.

The term "transition pH range" or "pH transition range" refers to a pH range over which the color of a particular sample or compound changes. A specific transition pH range for a sample may depend on a halochromic agent in the sample (see above).

The term "nucleic acid amplification" or "amplification reaction" refers to methods of amplifying DNA, RNA, or modified versions thereof. Nucleic acid amplification includes several techniques, such as an isothermal reaction or a thermocycled reaction. More specifically, nucleic acid amplification includes methods such as polymerase chain reaction (PCR), loop-mediated isothermal amplification (LAMP), strand displacement amplification (SDA), recombinase polymerase amplification (RPA), helicase dependent amplification (HDA), multiple displacement amplification (MDA), rolling circle amplification (RCA), and nucleic acid sequence-based amplification (NASBA). The term "isothermal amplification" refers to an amplification method that is performed without changing the temperature of the amplification reaction. Protons are released during an amplification reaction: for every deoxynucleotide triphosphate (dNTP) that is added to a single-stranded DNA template during an amplification reaction, one proton ($H^+$) is released.

The term "sufficient amount" means an amount sufficient to produce a desired effect, e.g., an amount sufficient to modulate protein aggregation in a cell.

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (www.ncbi.nlm.nih.gov/).

It must be noted that, as used in the specification and the appended claims, the singular forms "a," "an" and "the" include plural referents unless the context clearly dictates otherwise.

Compositions of the Invention

Disclosed herein are compositions and methods for accelerated and efficient colorimetric detection of nucleic acid amplification reaction products. In an embodiment, a colorimetric assay is used to visually detect the presence of an amplified nucleic acid product, which eliminates the need for expensive and sophisticated instrumentation.

In some embodiments, the colorimetric detection of amplification products is achieved by amplifying a target nucleic acid template molecule to obtain the amplification reaction product. The amplification reaction includes a reaction mix. In an embodiment, the reaction mix includes a nucleic acid template molecule, one or more enzymes for catalyzing the amplification reaction, and one or more halochromic agents for colorimetric detection. In a further embodiment, the reaction mix also includes a buffer having a buffering capacity equivalent to Tris buffer at a concentration between 1 mM-19 mM in a solution having a starting pH of 8.0. In further embodiments, the reaction mix also includes a plurality of nucleic acid primers, deoxynucleotide triphosphates (dNTPs), suitable salts for the enzyme, and other non-buffered chemicals that enable nucleic acid amplification.

During the amplification reaction, one proton is released for each dNTP that is incorporated into a nucleic acid template molecule. Thus, the pH of the reaction mix decreases throughout the amplification reaction. In an embodiment, if the target nucleic acid is present, the amplification reaction changes the starting pH of the reaction mix to cause a detectable colorimetric change of the halochromic agent, thereby indicating the presence of the target nucleic acid, and if the target nucleic acid is not present, the amplification reaction does not generate a sufficient number of protons to change the starting pH of the reaction mix sufficient to cause a detectable colorimetric change of the halochromic agent, thereby indicating that the amplification reaction product has not been produced. In an embodiment, the halochromic agent (or pH indicator) in the reaction mix has a transition pH range for a colorimetric change of the halochromic agent that is narrower than an expected pH change between (1) a starting pH of the reaction mix before the amplification reaction is performed, and (2) an ending pH of the reaction mix after the amplification reaction has been performed.

In an embodiment, the halochromic agent is a colorimetric agent or a fluorescent agent. Suitable halochromic agents include phenol red, bromocresol purple, bromothymol blue, neutral red, naphtholphthalein, cresol red, cresolphthalein, phenolphthalein, methyl red, and thymolphthalein, among others. A wide range of concentrations of these halochromic agents can be used in the reaction mix. Different halochromic agents have different transition pH ranges. In some embodiments, the halochromic agent has a transition pH range between pH 5-10, between pH 6-9, or between pH 6.5-8.8. In another embodiment, the halochromic agent is at a concentration between 25-100 µM in the reaction mix. In another embodiment, the halochromic agent is at a concentration between 50-260 µM. In some embodiments, a combination of two or more halochromic agents is used in the reaction mix, which increases the normalized color contrast change of the reaction mix by being of complementary colors at the beginning and similar colors at the end of the amplification reaction. In a further embodiment, the combination of halochromic agents comprises phenol red and bromothymol blue. In a further embodiment, the combination of halochromic agents comprises cresol red and bromothymol blue.

In one example, Phenol red is a halochromic agent that has a transition pH range from around 6.4-8.0. At the upper limit of the transition pH range, phenol red is red, and at the lower limit of the transition pH range, phenol red is yellow. A reaction mix containing phenol red will change color from red to yellow throughout the amplification reaction, as long as the starting pH of the reaction mix is around or above 8.0, and the ending pH of the reaction mix is within the transition pH range or around or below 6.4.

In some embodiments, the starting pH of the reaction mix is set by adding an acid or a base to the reaction mix until the desired starting pH is reached. The ending pH of the reaction mix is determined by performing a sample amplification reaction and measuring the ending pH (for example, with a micro-pH electrode). In an embodiment, the halochromic agent for an amplification reaction is selected so that the transition pH range lies in between the starting pH and ending pH. In a further embodiment, the halochromic agent is selected so that the transition pH range is nearer to the starting pH than the ending pH. The halochromic agent can also be selected based on the particular enzyme used for catalyzing the amplification reaction. Near the ending pH, the enzyme in the reaction mix terminates polymerization of the amplification reaction as the pH decreases to unfavorable $H^+$ concentrations. In an embodiment, additional hydronium ions or hydronium ion equivalents are added to the reaction mix via the sample. For example, between $4.8\times10^{-9}$ and $4.8\times10^{-18}$ additional hydronium ion equivalents per 10 µl reaction mix can be tolerated for the amplification reaction to proceed. In a further embodiment, between $4.8\times10^{-10}$ and $4.8\times10^{-18}$, $4.8\times10^{-12}$ and $4.8\times10^{-18}$, or $4.8\times10^{-15}$ and $4.8\times10^{-18}$ can be tolerated.

Generally, the enzyme will catalyze amplification reactions within a pH range that encompasses or is close to the transition pH range of the selected halochromic agent. Various enzymes can be used for the reaction, and different enzymes catalyze amplification reactions at different pH ranges. For example, Bst polymerase is believed to catalyze amplification reactions within the pH range of 6.6-9.0. The preferred starting pH for Bst polymerase is greater than 7, more preferably greater than 8.2, and more preferably at 8.8. Other examples of a preferred starting pH for Bst polymerase are found in U.S. Pat. No. 5,830,714, filed Apr. 17, 1996, hereby incorporated by reference in its entirety. In an embodiment, phenol red is coupled with Bst polymerase in a reaction mix, since the pH range at which Bst polymerase is active (6.6-9.0) encompasses the transition pH range of phenol red (6.4-8.0). In another embodiment, methyl red is coupled with U exo-Klenow fragment (polymerase for Helicase Dependent Amplification, HDA) in a reaction mix, since a starting pH at which U exo-Klenow fragment is active (around 7.5) is higher than the transition pH range of methyl red (4.8-6.2).

Other than Bst or Bst 2.0 polymerase, other enzymes capable of being used for catalyzing the amplification reaction include the polymerase from *Thermus aquaticus* (TAQ), DNA polymerases I-IV, Kapa Polymerase, RNA polymerases I-V, T7 RNA Polymerase, a reverse transcriptase, any DNA polymerase or RNA polymerase, a helicase, a recombinase, a ligase, a restriction endonuclease, and a single-strand binding protein. In some embodiments, an isothermal amplification reaction uses an enzyme that is a strand displacement polymerase, such as phi29-DNA-Polymerase, Klenow DNA-Polymerase, Vent DNA Polymerase, Deep Vent DNA Polymerase, Bst DNA Polymerase, 9oNm (TM) DNA Polymerase, U exo-Klenow fragment, or mutants and variants thereof. In some embodiments, suitable salts for the enzyme are also added to the reaction mix. In certain embodiments, the starting pH of the reaction mix is set based on an optimal pH for the specific enzyme used for catalyzing the amplification reaction. In an embodiment, the pH of the entire DNA sample is between pH 3 and pH 11.

In other embodiments, a fluorescent halochromic agent is used to detect protons released during amplification. The halochromic agent may change optical properties (such as amplitude and emitted wavelength) as the pH of the reaction mix changes during the amplification reaction. Fluorescent halochromic agents include fluorescein, pyranine, and pHrodo dye (Life Technologies, Carlsbad Calif.).

The base and/or acid added to the reaction mix maintains the starting pH of the reaction mix around or above an upper limit of the transition pH range of the halochromic agent. For example, an acid such as hydrochloric acid (HCl) or sulfuric acid ($H_2SO_4$), or a base such as sodium hydroxide (NaOH) or potassium hydroxide (KOH), can be added to the reaction mix. In some embodiments, the acid or base sets the starting pH of the reaction mix between pH 6-10, between pH 7-8, or between pH 8-8.6. In an embodiment, the reaction mix is capable of offsetting the starting pH of the reaction mix by less than 0.1 pH units. In another embodiment, the reaction mix has a starting pH lower than 2 pH units above the upper limit of the transition pH range of the halochromic agent. In further embodiments, the reaction mix has a starting pH lower than 1 pH unit, 0.5 pH units, or 0.1 pH units above the upper limit of the transition pH range of the halochromic agent. In a further embodiment, noise from non-specific amplification is minimized by setting the pH transition range sufficiently separated from the starting pH of the reaction mix, so that any color change is only achieved by a specific and sustained amplification.

In an embodiment, the reaction mix does not require any additional buffering agent for the amplification reaction, since a buffering agent could prevent large changes in pH from occurring during the amplification reaction. In another embodiment, the reaction mix contains a minimal amount of buffering agent, such that the buffering capacity of the reaction mixture is less than the expected change in pH during amplification. In some embodiments, the buffer is at a concentration between 1 mM and 3 mM. In a further embodiment, the buffer is at a concentration of 1 mM. In certain embodiments, the buffer used is Tris buffer (formulated to pH 8.8), HEPES (pH 7-9), or TAPS (pH 7-9). In another embodiment, the buffer used is a buffer having a buffering capacity equivalent to a Tris buffer at a concentration between 1 mM-19 mM in a solution having a starting pH of 8.0. This broad range of suitable buffer concentrations allows the reaction mix to resist unwanted starting pH changes during reaction setup, unlike reaction setups with minimal (<1 mM) Tris buffer equivalents (see U.S. Ser. No. 13/799,995, filed Mar. 13, 2013). These unwanted changes in pH come about due to hydronium or hydroxide ion equivalents added to the reaction via the sample reagents. As colorimetric detection and enzyme kinetics depend on the starting pH, the presence of buffer capacity in the reaction mix high enough to avoid starting pH change, but low enough to allow color change upon amplification, become important. In a further embodiment, the pH of the reaction mix is between pH 7.5-8.8. Table 1 shows various buffers having buffering capacities equivalent to a Tris buffer at a concentration between 1 mM-19 mM in a solution having a starting pH of 8.0. The buffer capacity ($\beta$) is defined as the equivalents of acid or base needed to change the pH of 1 Liter of buffer by 1 pH unit. This can be calculated as: $\beta=2.3*C*(K_a*[H_3O^+]/(K_a+[H_3O^+])^2)$; where C is the buffer concentration, $K_a$ is the dissociation constant for the buffer and $[H_3O^+]$ is the hydronium ion concentration of the buffer (which is calculated from the reaction starting pH). The buffer capacity of 1 mM-19 mM Tris (in a solution having a starting pH of 8.0) was found to range from 0.000575 to 0.010873. The starting pH of the buffer was considered to be in the range of 7.5-8.8 to be compatible with the reaction biochemistry (polymerase function, nucleic acid melting, etc.). In other embodiments, the buffer has a buffering capacity equivalent to a Tris buffer at a concentration between 1.5 mM-19 mM, 2 mM-19 mM, 3 mM-19 mM, 4 mM-19 mM, 5 mM-19 mM, 6 mM-19 mM, 7 mM-19 mM, or otherwise, in a solution having a starting pH of 8.0. In other embodiments, the buffer has a buffering capacity equivalent to a Tris buffer at a concentration between 1.92 mM-36.29 mM, 3 mM-36.29 mM, 4 mM-36.29 mM, 5 mM-36.29 mM, or otherwise, in a solution having a starting pH of 8.8. In other embodiments, the buffer has a buffering capacity equivalent to a Tris buffer at a concentration between 1.48 mM-27.92 mM, 2 mM-27.92 mM, 3 mM-27.92 mM, 4 mM-27.92 mM, 5 mM-27.92 mM, or otherwise, in a solution having a starting pH of 7.5.

TABLE 1

Buffer Capacity Table

| Buffer | Full Chemical Name | pKa at 25° C. | Starting Reaction pH | Min Conc (mM) | Max Conc (mM) |
|---|---|---|---|---|---|
| Tris | tris(hydroxymethyl)methylamine | 8.06 | 8.8 | 1.92 | 36.29 |
|  |  |  | 8.0 | 1.00 | 19.00 |
|  |  |  | 7.5 | 1.48 | 27.92 |
| TAPS | N-Tris(hydroxymethyl)methyl-3-aminopropanesulfonic acid | 8.43 | 8.8 | 1.19 | 22.55 |
|  |  |  | 8.0 | 1.27 | 23.94 |
|  |  |  | 7.5 | 2.66 | 50.25 |
| Bicine | N,N-bis(2-hydroxyethyl)glycine | 8.35 | 8.8 | 1.29 | 24.46 |
|  |  |  | 8.0 | 1.17 | 22.15 |
|  |  |  | 7.5 | 2.31 | 43.59 |
| Tricine | N-tris(hydroxymethyl)methylglycine | 8.15 | 8.8 | 1.67 | 31.63 |
|  |  |  | 8.0 | 1.03 | 19.48 |
|  |  |  | 7.5 | 1.67 | 31.63 |
| TAPSO | 3-[N-Tris(hydroxymethyl)methylamino]-2-hydroxypropanesulfonic acid | 7.635 | 8.8 | 4.17 | 78.90 |
|  |  |  | 8.0 | 1.19 | 22.45 |
|  |  |  | 7.5 | 1.02 | 19.37 |
| HEPES | 4-(2-hydroxyethyl)-1-piperazineethanesulfonic acid | 7.48 | 8.8 | 5.74 | 108.45 |
|  |  |  | 8.0 | 1.40 | 26.54 |
|  |  |  | 7.5 | 1.00 | 18.92 |
| TES | N-tris(hydroxymethyl)methyl-2-aminoethanesulfonic acid | 7.4 | 8.8 | 6.79 | 128.39 |
|  |  |  | 8.0 | 1.56 | 29.46 |
|  |  |  | 7.5 | 1.01 | 19.16 |
| MOPS | 3-(N-morpholino)propanesulfonic acid | 7.2 | 8.8 | 10.46 | 197.77 |
|  |  |  | 8.0 | 2.12 | 40.03 |
|  |  |  | 7.5 | 1.12 | 21.26 |

TABLE 1-continued

Buffer Capacity Table

| Buffer | Full Chemical Name | pKa at 25° C. | Starting Reaction pH | Min Conc (mM) | Max Conc (mM) |
|---|---|---|---|---|---|
| PIPES | 1,4-piperazinediethaiiesulfonic acid acid | 6.76 | 8.8 | 27.91 | 500.00 |
| | | | 8.0 | 4.86 | 91.88 |
| | | | 7.5 | 1.92 | 36.29 |
| SSC | Saline Sodium Citrate | 7.0 | 8.8 | 16.28 | 300.00 |
| | | | 8.0 | 3.03 | 57.20 |
| | | | 7.5 | 1.37 | 25.90 |

In an embodiment, a magnesium compound is added to the reaction mix, because magnesium promotes nucleotide incorporation into the template and influences the activity of the polymerase. In a further embodiment, the concentration of a magnesium compound (such as magnesium sulfate) in the reaction mix is at least 0.5 mM, at least 1 mM, at least 2 mM, or at least 4 mM. In an embodiment, the concentration of added magnesium ion is dependent on the concentration of dNTPs, nucleic acid template, and primers. In an embodiment, the ratio of dNTPs to magnesium sulphate in the reaction mix is less than 1:2, less than 1:3, less than 1:4 or less than 1:5.

In some embodiments, monovalent cations are added to the reaction mix. Monovalent cations include potassium, ammonium, and quaternary ammonium, among others. Monovalent cations can affect the melting characteristics of the nucleic acid template and improve the efficiency of the enzyme. In an embodiment, potassium is in the reaction mix at a concentration of less than 50 mM, or less than 15 mM. In another embodiment, quaternary ammonium salts are in the reaction mix at a concentration of greater than 2 mM, greater than 5 mM, or greater than 8 mM. In another embodiment, an ammonium compound (such as ammonium chloride) is in the reaction mix at a concentration of less than 15 mM, or less than 10 mM. Ammonium ($NH_4^+$) has some buffering capability, thus the final concentration of ammonium compounds in the reaction mix should be minimized while maintaining optimal amplification yield.

In an embodiment, the concentrations of other reagents of the reaction mix are kept at amounts as generally used in amplification reactions. See Notomi T et. al. Nucleic Acids Res. 2000 Jun. 15; 28(12): E63; Nature Protocols 2008, Loop-mediated isothermal amplification (LAMP) of gene sequences and simple visual detection of products, 2008 3(5): pg 880, hereby incorporated by reference in its entirety. In an embodiment, the Bst or Bst 2.0 enzyme is used, and the amount of enzyme is at least 0.8 Unit per microliter of combined fluid. In this embodiment, Betaine is also present in the reaction mix at a concentration between 0-1.5 M or 0.8M-1 M, and the total concentration of primers is between 3.6 µM and 6.2 µM. In some embodiments, any of the following reagents is present in the reaction mix: Tris buffer (pH 8.8) at 20 mM, KCl at 10 mM, $MgSO_4$ at 8 mM, $(NH_4)_2SO_4$ at 10 mM, Tween 20 at 0.1%, Betaine at 0.8 M, dNTPs at 1.4 mM each, $MnCl_2$ at 0.5 mM, FIP at 1.6 µM, F3 at 0.2 µM, B3 at 0.2 µM, primers at a total concentration of 5.2 µM (2*(1.6+0.8+0.2), and Bst/Bst 2.0 at 8 U per 10 µL.

The above reagent concentrations have been found to provide good amplification yield and low buffering capacity so that a halochromic pH sensor can be used to detect protons released during the amplification reaction. In some embodiments, the concentrations of reaction mix reagents depend on the enzyme selection. In further embodiments, guidance regarding appropriate reagent concentrations is available from the enzyme manufacturers. In an embodiment, the ratio of the sample volume to the reaction mix volume is such that the sample is diluted between 5% and 40% when the reaction mix is added.

In some embodiments, amplification reaction reagents are stored separately before being added to a reaction mix, since some reagents have specific required conditions for stability. For example, the enzyme may be stored long term in a moderately buffered solution separate from the other reagents to ensure stability of the enzyme. Upon mixing with the remaining reagents in the reaction mix, the buffering agent becomes sufficiently diluted so as not to significantly mask a pH change. In addition, primers for specific genes of interest may be provided in a separate solution or in a lyophilized form.

In some embodiments, the amplification reaction is performed within a microtube. In other embodiments, the amplification reaction is performed within a fluidic or microfluidic structure. In some embodiments, the fluidic or microfluidic structure is a well, chamber, or channel that receives the reagents and the nucleic acid sample separately, and then mixes the components together. In another embodiment, the fluidic or microfluidic structure is a well, chamber, or channel that receives the pre-mixed reaction mix. In a further embodiment, the fluidic or microfluidic structure possesses a long optical path for colorimetric observation, or a fluorescent/absorbance excitation source and detector. In another embodiment, the fluidic or microfluidic structure receives the reagents in a lyophilized form, and subsequently receives the nucleic acid sample and hydration solution. In an embodiment, a chamber fluidic or microfluidic structure has a channel depth ranging between 50 µm-400 µm or greater. In a further embodiment, colorimetric observation is accomplished for channel depths (path length) of 50 µm, 50 µm-400 µm, or 50 µm or greater.

Some embodiments include a kit for colorimetric detection of an amplification product. The kit may include one or more halochromic agents, one or more enzymes for catalyzing an amplification reaction, and instructions for contacting a sample with a reaction mix including the buffer and the enzyme and the halochromic agent under conditions that an amplification reaction occurs and produces an amplification reaction product if the sample contains a target nucleic acid template molecule, the reaction mix having a starting pH, and if the target nucleic acid template molecule is present, the amplification reaction changes the starting pH of the reaction mix to cause a detectable colorimetric change of the halochromic agent, thereby indicating the presence of the target nucleic acid, and if the target nucleic acid template molecule is not present, the amplification reaction does not generate a sufficient number of protons to change the starting pH of the reaction mix sufficient to cause a detectable colorimetric change of the halochromic agent, thereby indicating that the amplification reaction product has not been produced. In another embodiment, the instructions are for contacting a nucleic acid template molecule with the halochromic agent and enzyme in a reaction mix, under conditions that result in (1) an amplification reaction that amplifies the nucleic acid template molecule to produce an amplification reaction product, and (2) generation of a sufficient number of protons so that an ending pH of the reaction mix is sufficiently low to produce a detectable colorimetric change of the halochromic agent, thereby indicating that the amplification reaction product has been produced. In further embodiments, the kit also includes an acid or base, dNTPs, primers, and monovalent cations. In a further embodiment, the kit includes the following reagents at the following concentrations:

Bst or Bst 2.0 polymerase, at least 0.8 Unit per microliter;
Betaine at 0.8 M;
Primers at 3.6 µM total;
  FIP and BIP primers at 1.6 µM
  F3 and B3 at 0.2 µM
Magnesium sulfate at 8 mM;
Ammonium sulfate at 10 mM;
Potassium chloride at 10 mM;
Sodium hydroxide to set the starting pH of the reaction mix;
Tween20 at 0.1%;
dNTP's at 1.4 mM each;
Phenol red at 50 µM.

In a further embodiment, the kit includes LoopF and LoopB primers at 0.8 µM each.

Methods of the Invention

The amplification reaction amplifies nucleotides from a nucleic acid template. In some embodiments, the amplification reaction is an isothermal amplification reaction, such as a strand displacement reaction. In a further embodiment, a strand displacement reaction is provided by a polymerase with strand displacement activity under reaction conditions such that strand displacement is possible. Examples of strand displacement reactions include strand displacement amplification (SDA), multiple displacement amplification (MDA), rolling circle amplification (RCA) or loop mediated isothermal amplification (LAMP). In other embodiments, the amplification reaction includes other non-isothermal amplification reactions such as polymerase chain reaction (PCR).

In certain embodiments, the amplification reaction performed is LAMP. In a LAMP reaction, a double- or single-stranded DNA template in dynamic equilibrium at an elevated temperature is amplified using two or three pairs of primers. The primers are designed based on the DNA template, using primer design software such as LAMP Designer (Premier Biosoft, Palo Alto, Calif.). In the first step of the LAMP reaction, the F2 region of the FIP (Forward Inner Primer) anneals to the single stranded DNA at the respective complementary (F2c) position. Next, a polymerase with strand displacement activity incorporates dNTPs along the template from the 3' end of F2. The incorporation of nucleotides releases protons, reducing the pH of the reaction mix. Then, the F3 forward primer anneals to the F3c region upstream of the F2 region and on the template. The F3 forward primer begins amplifying the template strand, which releases further protons and displaces the FIP-incorporated strand that was synthesized previously. This single strand contains an F1 sequence (within the target sequence) along with its complementary F1c sequence (within the FIP). This forms a stem-loop as F1c anneals to F1 at the 5' end. At the same time, the BIP (Backward Inner Primer) anneals to the other end of the strand and nucleotides extend from B2, releasing more protons. The backward primer B3 then binds to the B3c region, downstream of the B2 region, displaces the BIP-amplified strands and promotes extension to create the double strand. This displaced strand now contains a B1 sequence (within the target sequence) along with its complementary B1c sequence (within the BIP), forming another stem loop in the 3' end. The structure now has two stem-loop structures at each end from which continuous displacement and extension occur to amplify the template. The LAMP reaction can be amplified by adding further Forward and Backward Loop primers to produce more amplicons with stem loop structures.

The LAMP procedure can take place at a fixed temperature, minimizing the need for any expensive thermocycling equipments. Typically, isothermal methods require a set temperature, which is determined by the selected reagents. For example, enzymes function best between 60-65° C. in LAMP methods.

Colorimetric detection of the nucleic acid amplification reaction product can be performed in real-time throughout the amplification reaction, or after the performance of the amplification reaction. Detection of the colorimetric change of the reaction mix can be associated with a digital indication of a presence or absence of the amplification reaction product. In other words, a visual observation of the color change of the reaction mix can provide information regarding whether the amplification reaction product is present or absent. In certain embodiments, detection of a colorimetric change of the reaction mix indicates that the exponential or plateau phase of the amplification reaction has been obtained.

In some embodiments, detection of the amplification reaction product is accelerated relative to an amplification reaction that uses a reaction mix without a halochromic agent. In further embodiments, the colorimetric change of the reaction mix is detected in less than 60 minutes from a starting time of the amplification reaction. Accelerated detection of the amplification reaction product is obtained because the halochromic agent (a weak acid or base) in the reaction mix absorbs protons generated during the amplification reaction, and recombination of the free protons acts to accelerate the detection of the amplification reaction. The reaction can be designed so that minimal amplification is required to generate a pH transition sufficient for the halochromic agent to change color. Conventional amplification techniques that use fluorescent intercalating dyes, molecular beacons, hybridization probes, dye-based detection, UV-Vis, or other detection methods require a certain threshold amount of amplification to occur before an amplification signal is detectable. However, the methods of the present invention require a relatively smaller threshold amount of amplification before a color change of the halochromic agent is detectable, and therefore the detection of an amplification reaction product is accelerated relative to conventional amplification methods.

In some embodiments, the amplification reaction product is detected visually by observation of a color change of the reaction mix. In a further embodiment, the human eye is used for the visual detection. In another embodiment, a camera, a computer, or some other optical device is used for the visual detection or for imaging the reaction mix. Imaging programs include Photoshop (Adobe, San Jose Calif.), ImageJ (National Institutes of Health, Bethesda Md.), and MATLAB (MathWorks, Natick Mass.). In another embodiment, the amplification reaction product is detected by measuring fluorescence of the reaction mix, using fluorescence spectroscopy methods. In another embodiment, the amplification reaction product is detected by measuring absorbance of the reaction mix, using absorption spectroscopy methods. In a further embodiment, the endpoint or overall change in absorbance or fluorescence of the reaction mix is measured at a given wavelength or set of wavelengths.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, Biochemistry (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* $3^{rd}$ *Ed*. (Plenum Press) Vols A and B (1992).

Example 1: Colorimetric Detection of a Nucleic Acid Amplification Reaction Product In an assay for colorimetric detection of a nucleic acid amplification reaction product, the following reagents were mixed together to produce a 2× reagent mix:
Magnesium Sulphate (Sigma Aldrich) at 16 mM
Ammonium Sulphate (Sigma Aldrich) at 20 mM
Potassium Chloride (Sigma Aldrich) at 20 mM
Sodium hydroxide (Sigma Aldrich) at a concentration that sets the starting pH of the reagent mix to 8.8 pH The reagent mix was adjusted to an initial pH of 8.8 to enable efficient initial polymerization. The reagent mix was autoclaved for 1 hour for sterilization. The following ingredients were then added (in a sterile form) to the reagent mix to generate the reaction mix:
Tween20 (Sigma Aldrich) at 0.1% (v/v)
dNTPs (NEB) at 1.4 mM each
Phenol Red (Sigma Aldrich) at 50 μM
Bst polymerase (NEB) at 0.8 Unit per microliter (the enzyme storage buffer contributing 1 mM Tris buffer, 5 mM KCl, 0.01 mM EDTA, 0.1 mM DTT, 0.01% Triton X-100 (v/v) and 5% Glycerol ((w/v) to the reaction mix)
Betaine (Sigma Aldrich) at 0.8 M Primers and a nucleic acid template were added to the reaction mix. The primers were designed for LAMP and included two pairs of primers (solubilized in 1×Tris EDTA buffer) at a total concentration of 3.6 μM as described above. Primer F3 has the sequence: GATCTGAATCCGAC-CAACCG (SEQ ID NO: 1); primer B3 has the sequence: AACGCCCACGCTCTCGCA (SEQ ID NO: 2); the primer FIP has the sequence: AAATCCGTCCAGTGGTTTTTTT-GAAAATCGTTGTATCTCCG (SEQ ID NO: 3); and the primer BIP has the sequence: CCGAAACCACTGGACG-GATTTTTATTTTTAATCTAAAACAAACATC (SEQ ID NO: 4). The nucleic acid template molecule was purified from *Schistosoma mansoni*. FIG. 1 shows the SM1-7 target region of the nucleic acid template molecule (see Hamburger et al, Detection of *Schistosoma mansoni* and *Schistosoma haematobium* DNA by Loop-Mediated Isothermal Amplification: Identification of infected Snails from Early Prepatency, *Am J Trop Med Hyg*, 2010). The positive test reactions contained template DNA, and the negative control reactions contained water. The reaction mixes had a starting pH in the range of 7.5-8.5. The reaction mixes were heated in micro-tubes to 63° C. on a thermocycler to allow template amplification. After a predetermined reaction period of 45 minutes, during which sufficient template amplification occurred, the resultant color of the reaction mix was visually observed.

Figure 2:
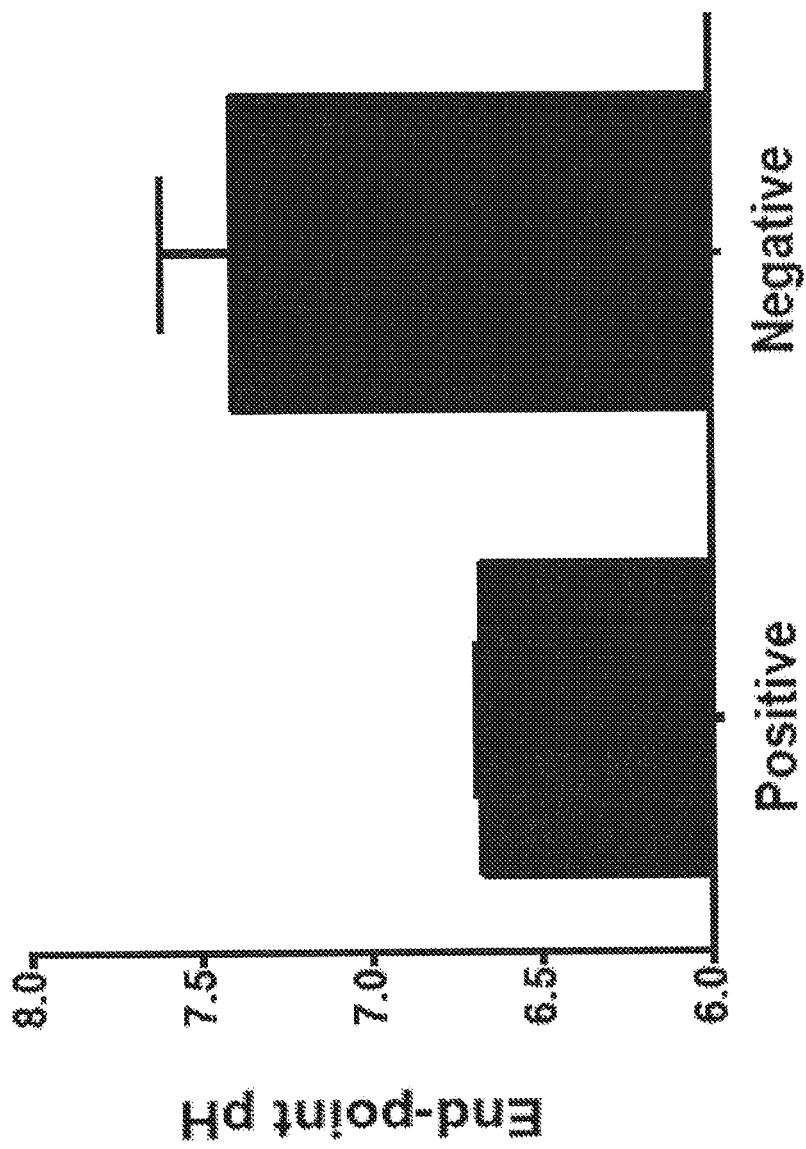
FIG. 2 is a graph indicating pH measurements for positive and negative isothermal amplification reactions, according to an embodiment.
Figure 3:
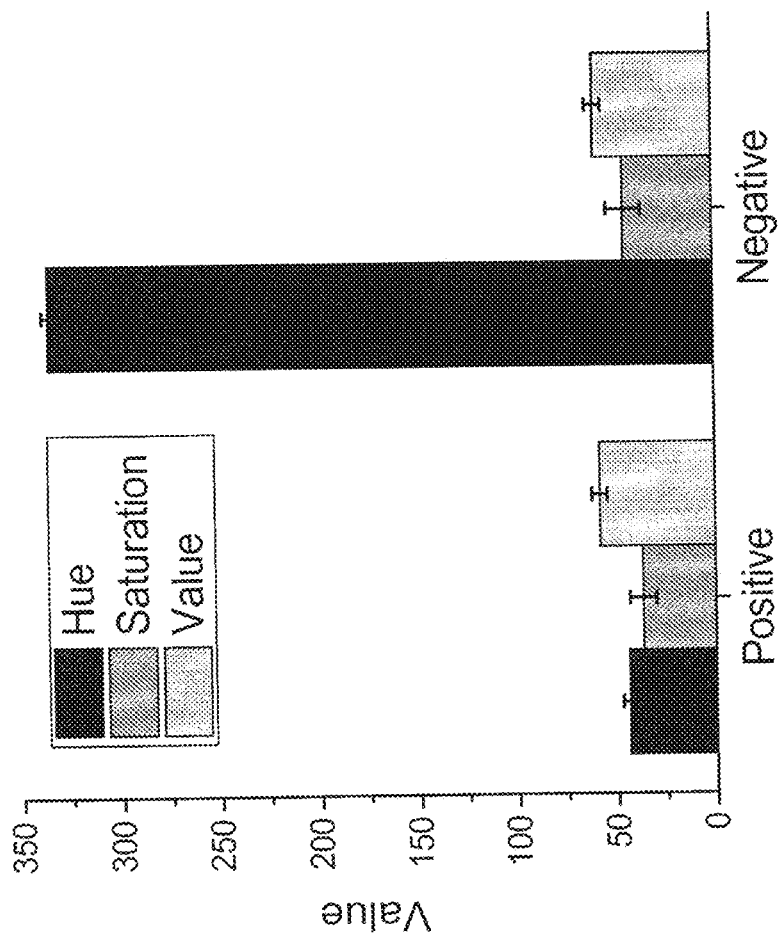
FIG. 3 is a graph showing the detection of color (hue) of positive and negative isothermal amplification reactions at the reaction endpoints, according to an embodiment.
Figure 4:
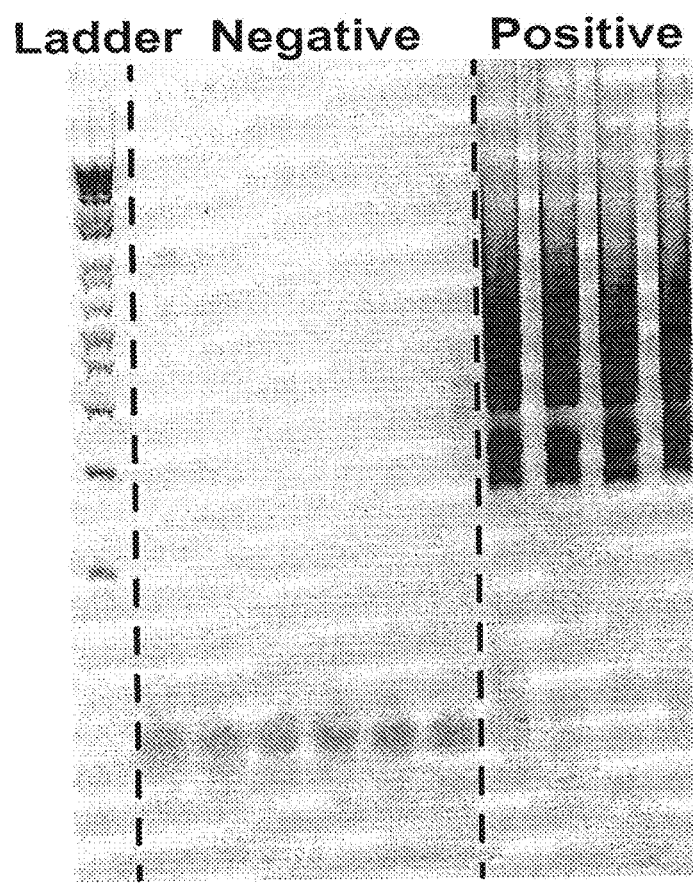
FIG. 4 shows the results of a gel electrophoresis assay of positive and negative isothermal amplification reaction products, according to an embodiment.

During the amplification process, the pH of the reaction mix was reduced from 7.5-8.5 to around 6.6 in a repeatable fashion. FIG. 2 is a graph showing the pH measurements for repeated positive (test) and negative (negative control) amplification reactions. The halochromic agent used was Phenol red, which has a transition pH range of 6.8-8.2. Phenol red changes color over this transition pH range from red to yellow (when the pH is lowered from the upper pH limit to the lower pH limit). In the assay, the reaction mix changed color from red (at pH 8.0) to yellow (at pH 6.6) in response to the pH change during nucleic acid amplification. FIG. 3 is a graph showing the difference in contrast value using HSV (hue, saturation, value) of images of the reaction mixes of a positive and negative amplification reaction at the reaction endpoints. The color change is quantitatively demonstrated in the hue variable. To confirm that the color change was due to target DNA amplification, endpoint reactions were analyzed using gel electrophoresis to verify the presence of amplicons (FIG. 4).

Using this method, amplification of a DNA template can be easily observed, either at the reaction end-point or in real-time throughout the reaction, by visually observing the color change in the reaction mix, or by measuring the absorbance or fluorescence of the reaction mix. This mechanism generates much larger contrast in comparison to other colorimetric detection techniques and can be imaged without the need of expensive optical instrumentation.

Example 2: Detection of LAMP Amplification Using a Visual Halochromic Agent

LAMP reactions were performed with a reaction mix comprising of: 10 mM $(NH_4)_2SO_4$, 15 mM KCl, 0.1 mM EDTA, 0.1 mM DTT, 0.01% Triton X-100 (v/v), 5% Glycerol, 8 mM $MgSO_4$, 1.4 mM each dNTPs, 0.1% v/v Tween-20, 0.8 M Betaine. Three primer pairs, specific to different targets, were added to a final concentration of 1.6 μM each for FIP/BIP, 0.2 μM each for F3/B3, 0.4 μM each for LoopB/F. The final reaction volume is 10 μL and was held at 63° C. for different incubation times.

Figure 5:
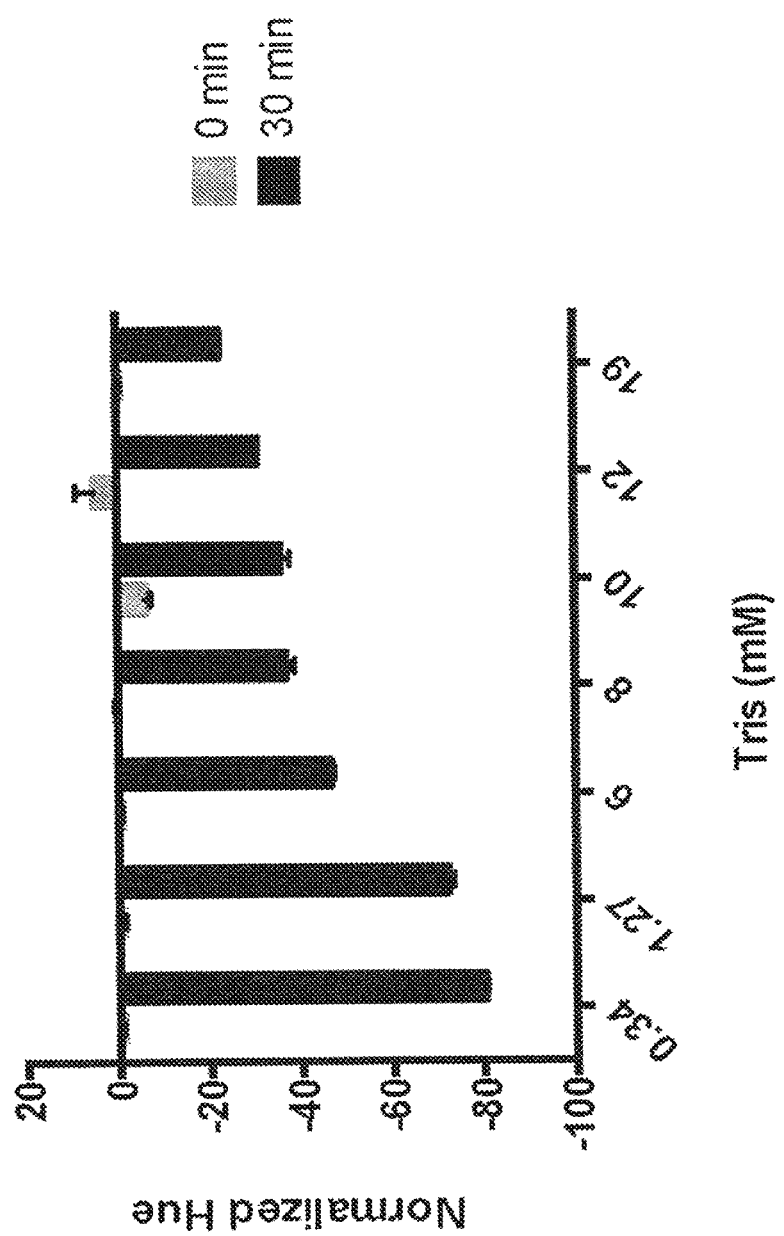
FIG. 5 shows the normalized hue values for amplification reactions using various Tris buffer concentrations, according to an embodiment.

In FIG. 5, the final Tris buffer concentration of the reaction mix was varied from 0.34 mM to 19 mM (by varying amount of Tris buffer formulated to pH 8.8). Reactions were performed with primers for lambda phage DNA, 5 ng of lambda DNA (New England Biolabs), 0.8 U/μl Bst 2.0 DNA polymerase (New England Biolabs) and 0.2 mM Neutral Red (Sigma Aldrich). The reaction tubes were then imaged and the Normalized Hue value was calculated for the color of the reaction mix. The Normalized Hue value was defined as the difference in Hue values between a positive and a no-template negative reaction. A color change, indicated by a change in the Normalized Hue value above the visualization threshold (dotted line), was observed for buffer concentrations as high as 19 mM Tris. This indicates that reaction mix with buffer capacities equivalent to >1 mM and <19 mM Tris allow enough pH change for visual color change detection.

Figure 6:
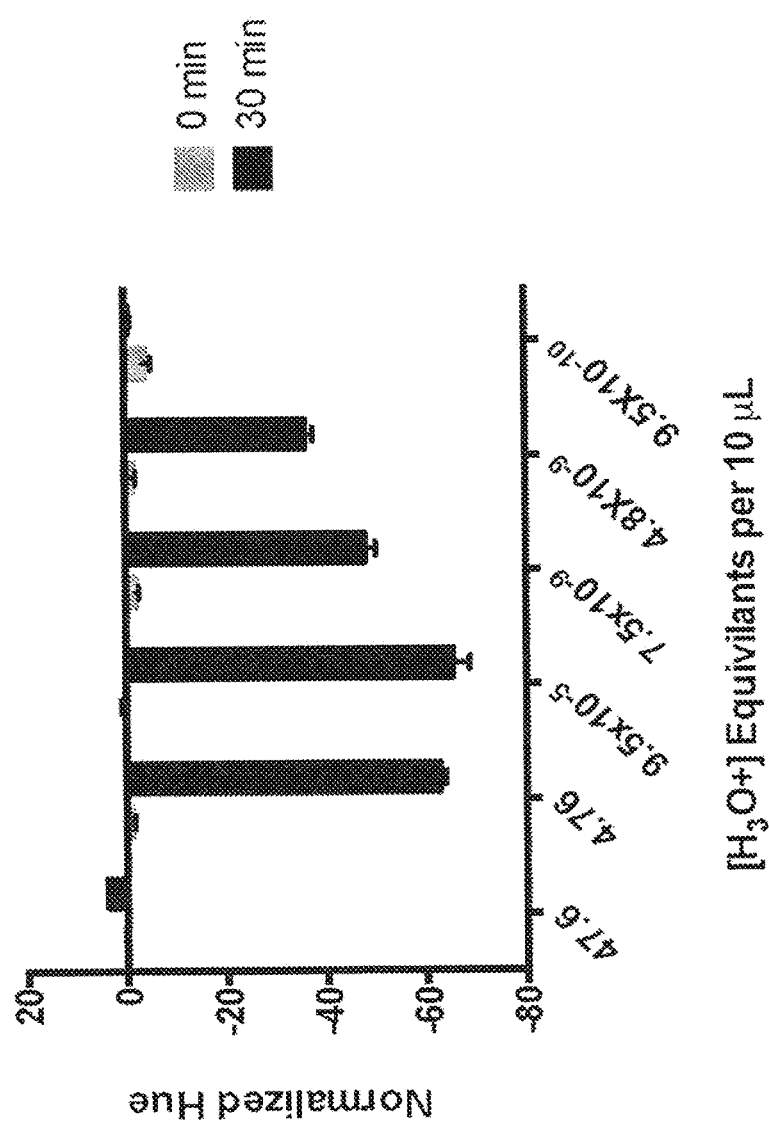
FIG. 6 shows the normalized hue values for amplification reactions using varying amounts of additional hydronium ion equivalents, according to an embodiment.

In FIG. 6, the tolerance of this visual detection method to excess hydronium ions added to the reaction mix was evaluated. This tolerance is important to allow the use of a wide variety of DNA samples which can add a range of hydronium or hydroxide ion equivalents to the reaction. Reactions were performed with 2 mM final Tris buffer concentration, 5 ng lambda DNA target, 0.8 U/μL Bst DNA polymerase and 0.2 mM Neutral Red halochromic agent. The change in Normalized Hue value indicates that this visual detection chemistry works with $4.8 \times 10^{-9}$ till $4.8 \times 10^{-18}$ additional hydronium ion equivalent per 10 uL reaction.

Figure 7A:
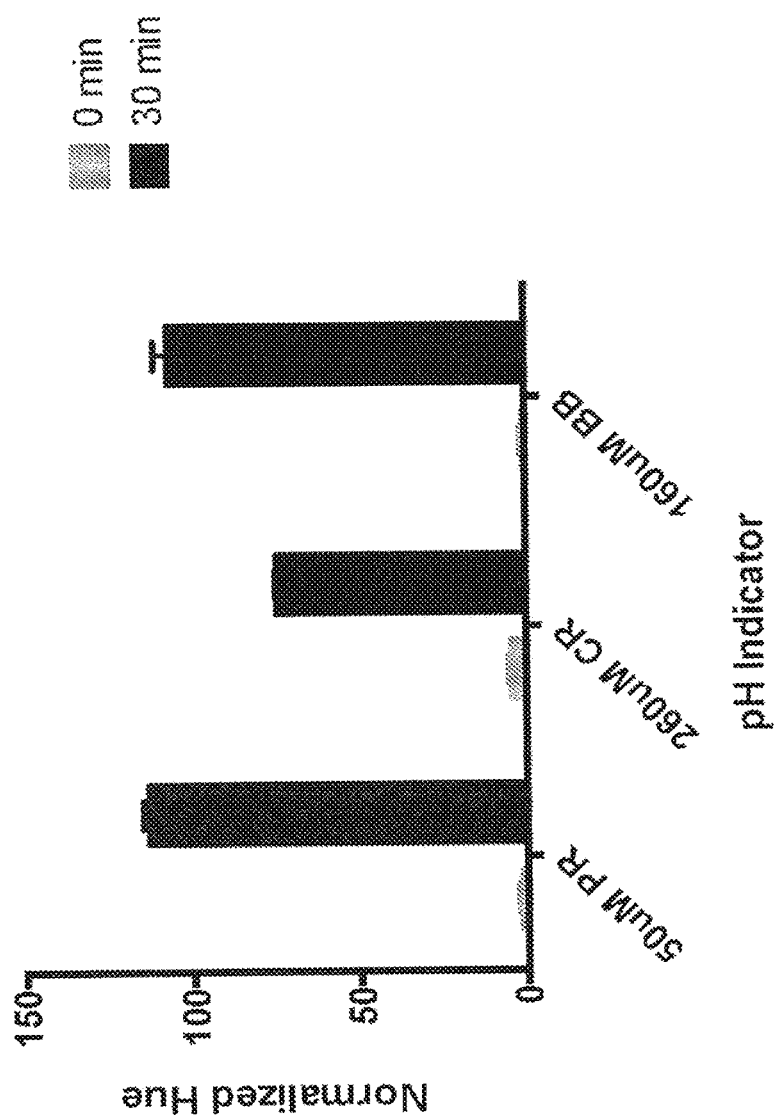
Figure 7B:
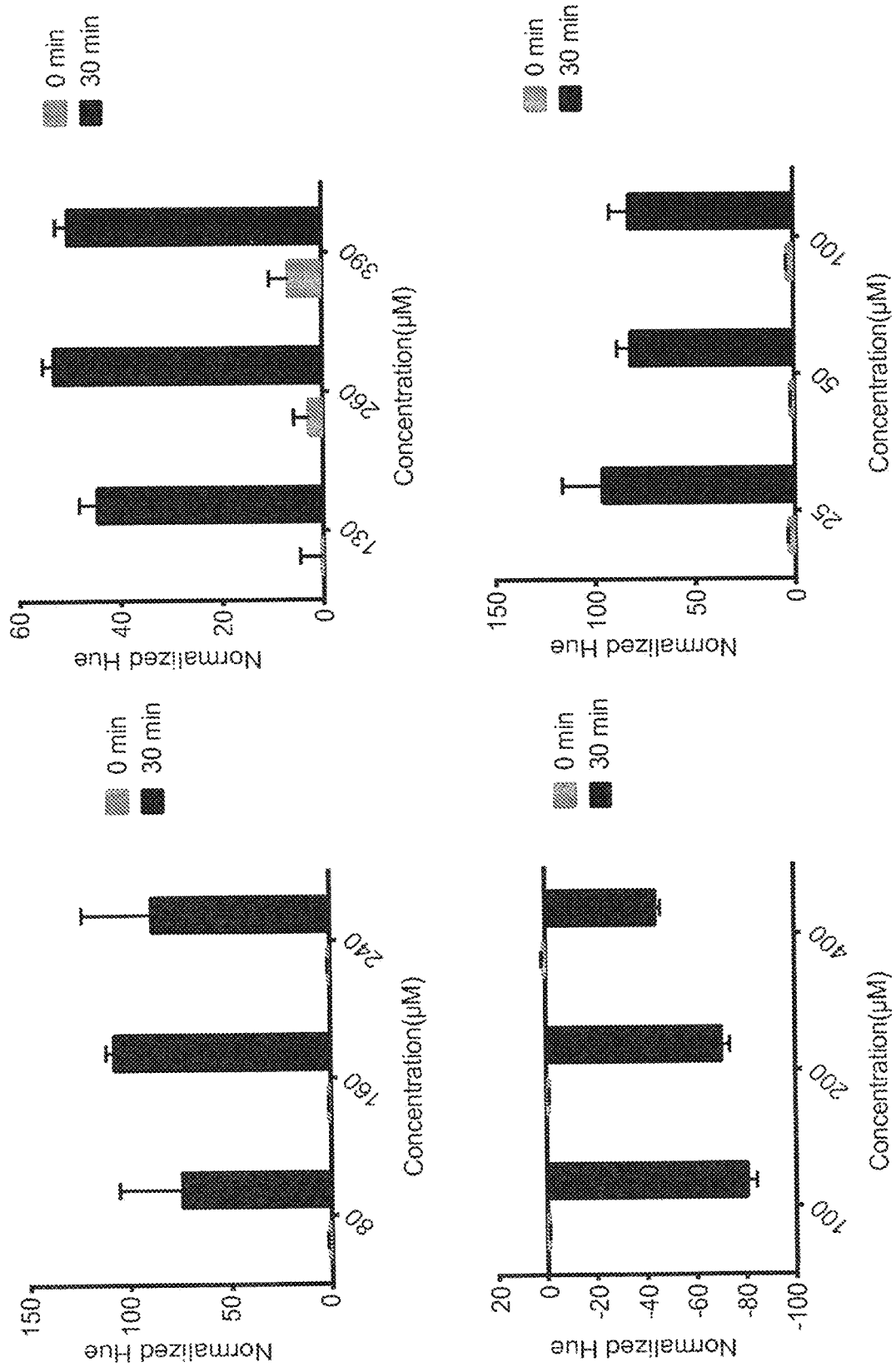
Figure 7D:
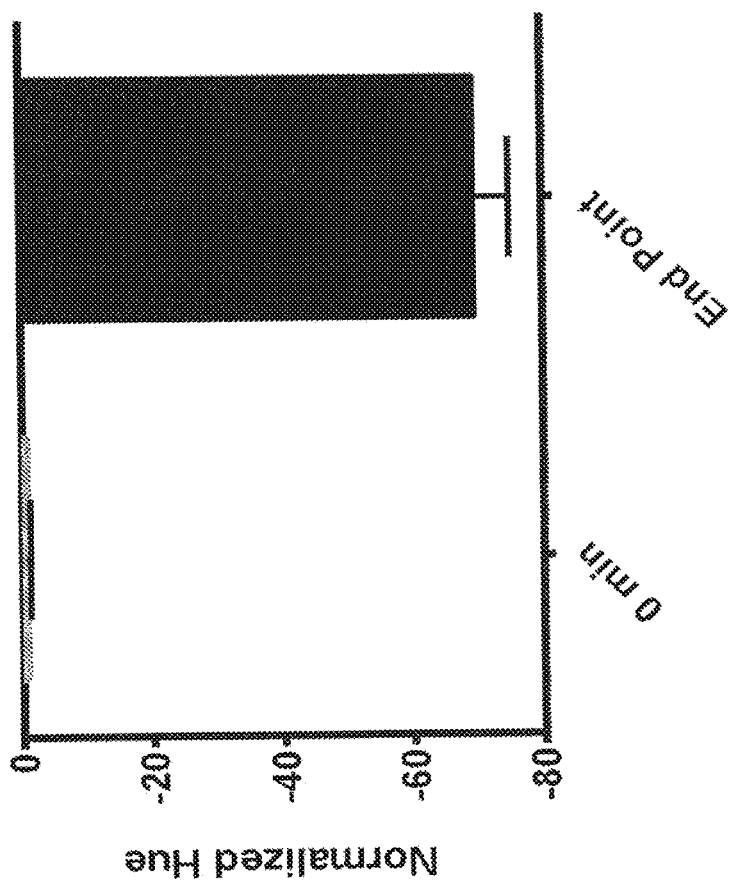

In FIGS. 7A-7D, the compatibility of different pH indicators and amplification targets with visual detection of LAMP amplification was evaluated. The reactions were performed with final Tris buffer concentration in the range of 1.2-1.3 mM and 0.8 U/μL Bst DNA polymerase. Three different indicator were tested with 5 ng lambda DNA target: 50 μM Phenol Red, 260 μM Cresol Red and 160 μM Bromothymol Blue (FIG. 7A). High contrast change in the normalized hue value was observed for all indicators tested.

Concentration sweeps were also performed for these indicators Bromothymol Blue (FIG. 7B top left), Cresol Red (FIG. 7B top right), Neutral Red (FIG. 7B bottom left) and Phenol Red (FIG. 7B bottom right) with Lambda target, which demonstrated the wide range of concentrations that are compatible with the chemistry. LAMP assays using 130 ng *Schistosoma mansoni* gDNA with 50 μM Phenol Red (FIG. 7C) and Human GAPDH mRNA with 0.2 mM Neutral Red (FIG. 7D) were also tested visual detection of these targets was demonstrated at end-point.

Figure 8:
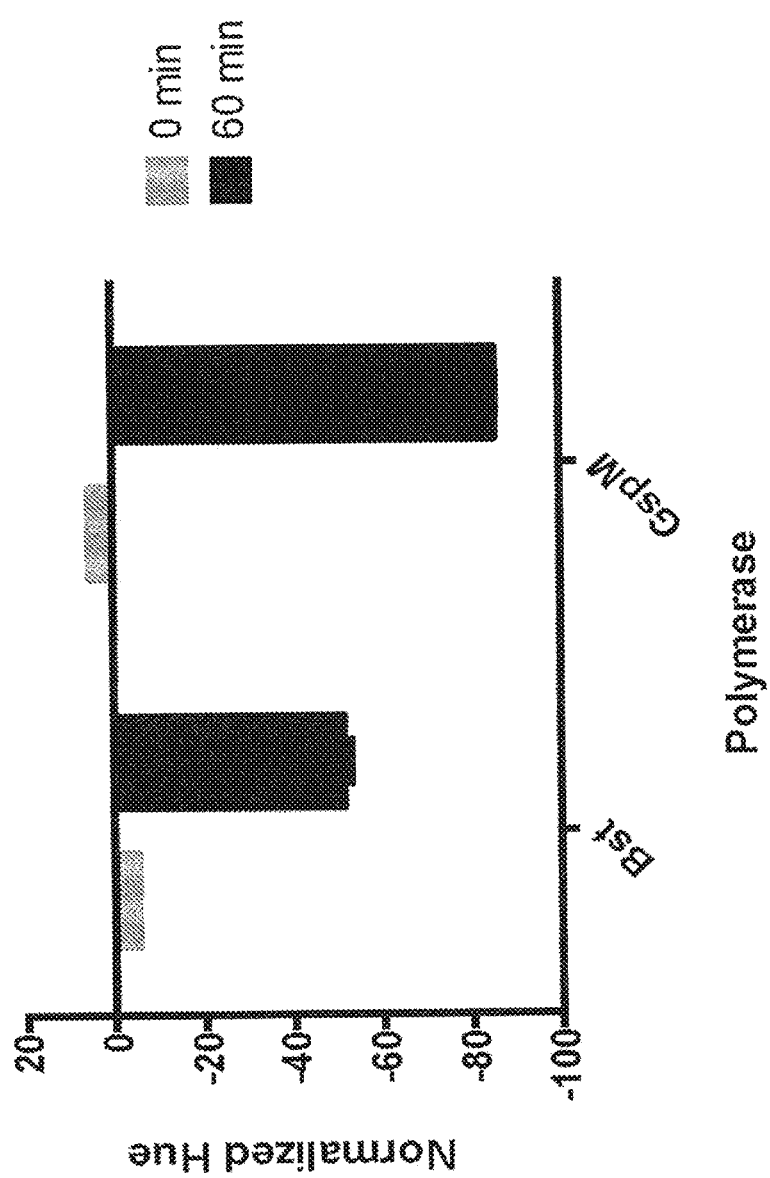
FIG. 8 shows the compatibility of different polymerases with visual detection of LAMP amplification, according to an embodiment.

In FIG. 8, the compatibility of different polymerases with visual detection of LAMP amplification was evaluated. The reactions were performed with 1.3 mM final Tris buffer concentration, 5 ng lambda DNA target and 0.2 mM Neutral Red. 0.8 U/μl of two different polymerases, Bst 2.0 and Gspm 2.0 (OptiGene), were used. High contrast color change was observed for both polymerases after 60 minutes of incubation (FIG. 8).

TABLE 2

Sequences Used

| | |
|---|---|
| Lambda FIP | SEQ ID NO: 5 |
| Lambda BIP | SEQ ID NO: 6 |
| Lambda F3 | SEQ ID NO: 7 |
| Lambda B3 | SEQ ID NO: 8 |
| Lambda Loop F | SEQ ID NO: 9 |
| Lambda Loop B | SEQ ID NO: 10 |
| Schistosoma F3 | SEQ ID NO: 1 |
| Schistosoma B3 | SEQ ID NO: 2 |
| Schistosoma FIP | SEQ ID NO: 3 |
| Schistosoma BIP | SEQ ID NO: 4 |
| GAPDH F3 | SEQ ID NO: 11 |
| GAPDH B3 | SEQ ID NO: 12 |
| GAPDH FIP | SEQ ID NO: 13 |
| GAPDH BIP | SEQ ID NO: 14 |
| GAPDH Loop F | SEQ ID NO: 15 |
| GAPDH Loop B | SEQ ID NO: 16 |

Figure 9A:
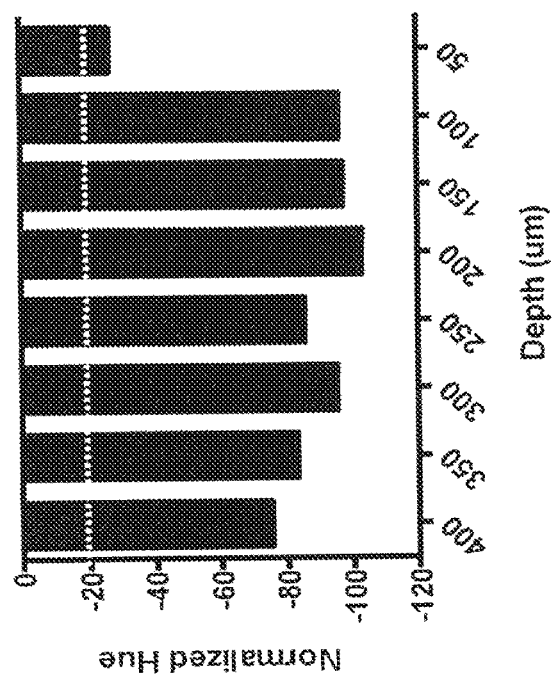
FIGS. 9A and 9B show the normalized hue values for amplification reactions using varying channel depths, according to an embodiment.
Figure 9B:
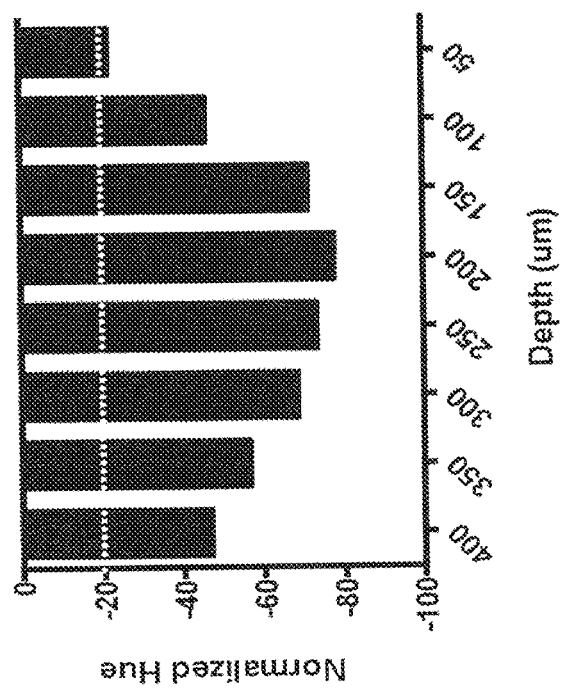

Example 3: Visual Detection of LAMP Amplification in Sub-Millimeter Path Lengths LAMP reactions were performed as in Example 1 with 1.3 mM final Tris buffer concentration (buffer formulated to pH 8.8), 0.8 U/μl of Bst 2.0 DNA Polymerase, 5 ng lambda DNA template and 0.2 mM Neutral Red or 160 μM Bromothymol Blue. Both the positive and the no-template negative reactions were added after amplification to flow chambers with varying channel depths (FIG. 9A for Neutral Red and FIG. 9B for Bromothymol Blue). These flow chambers were machined in acrylic with channel depths ranging from 50 μm to 400 μm. High contrast color difference (above the visual detection threshold; dotted line) between the positive and the negative reactions was observed for channel depths of 50 μm and above. This demonstrates that this visual detection chemistry is amenable for use in reaction chambers with sub-milimeter path lengths (depths) and above. Such reaction chambers can be used to reduce the amount of reagents used and to allow multiple reactions to take place in a certain footprint (eg. in a microfluidic cartridge).

Figure 10:
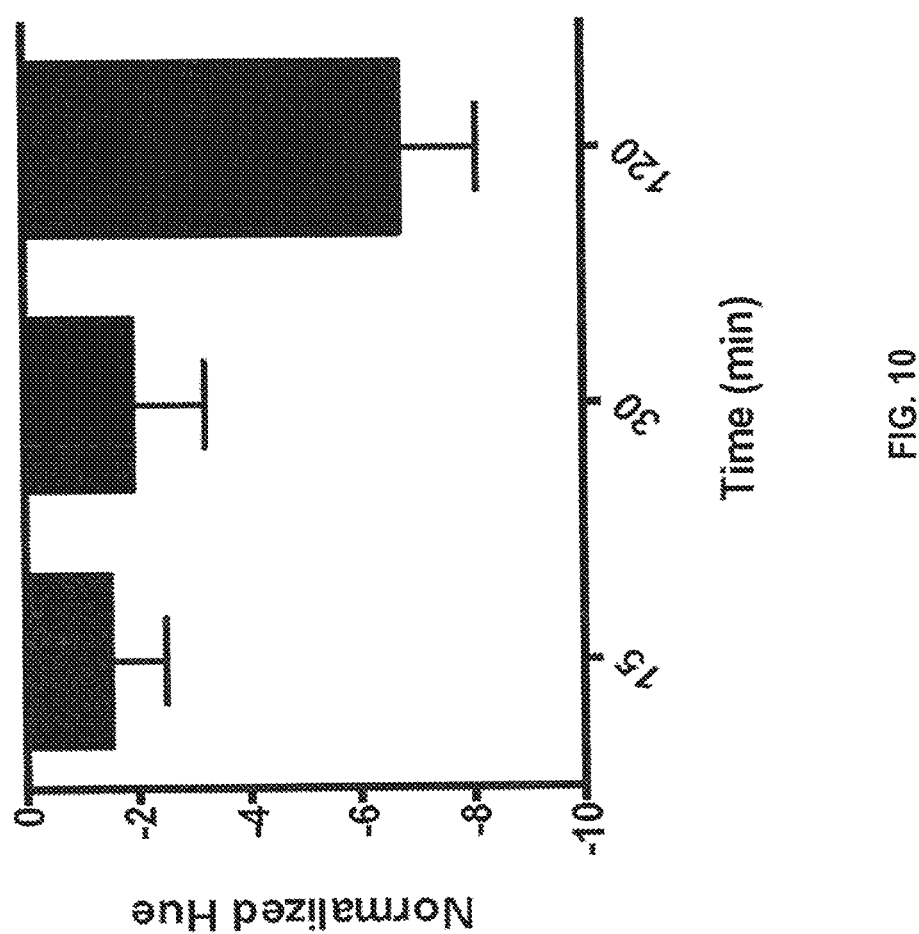
FIG. 10 shows the normalized hue values over time for SDA, according to an embodiment.

Example 4: Detection of Strand Displacement Amplification (SDA) Using a Visual Halochromic Agent SDA reactions were performed using a reaction mix comprising of: 1.3 mM final Tris buffer concentration (buffer formulated to pH 8.8), 10 mM $(NH_4)_2SO_4$, 50 mM KCl (adjusted to pH 8.5), 8 mM $MgSO_4$, 4.4 mM each dATP, dGTP, dTTP, 0.8 mM dCTP-aS (TriLink Biotechnologies), 0.1% v/v Tween-20, 0.8 M Betaine, 0.32 U/μl Bst DNA polymerase (New England Biolabs), 0.2 U/uL BSoBI (New England Biolabs) and 0.2 mM Neutral Red halochromic agent. Primers designed for human BRCA1 (SDAf: SEQ ID NO: 17; SDAr: SEQ ID NO: 18; BF: SEQ ID NO: 19; BR: SEQ ID NO: 20) were added to the reaction at 0.5 μM final concentration each. 5 ng of HeLa gDNA was added to a final reaction volume of 25 μL and was held at 65° C. for different incubation times. A change in Normalized Hue value over time (FIG. 10) indicates that this visual detection chemistry works with SDA.

Example 5: Detection of PCR Amplification Using a Visual Halochromic Agent

Figure 11:
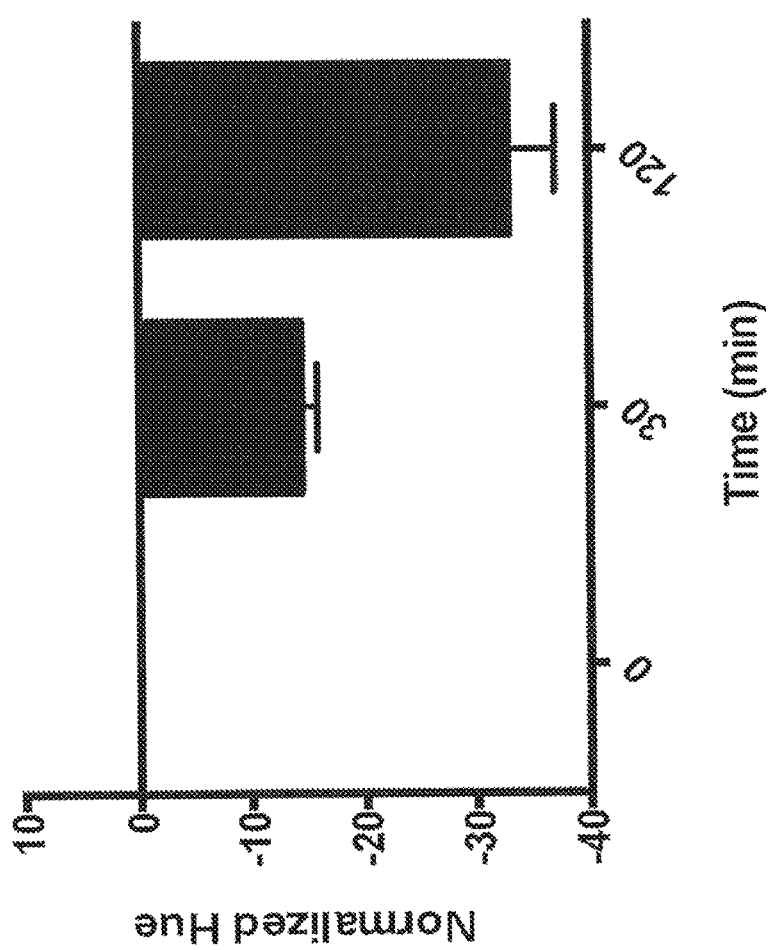
FIG. 11 shows the normalized hue values over time for PCR, according to an embodiment.

PCR reactions were performed using a reaction mix comprising of: 50 mM KCl and 2 mM $MgCl_2$ (pH adjusted 8.5), 0.5 mM each dNTP, 5 U Taq DNA polymerase (New England Biolabs) and 0.2 mM Neutral Red halochromic agent. Total carry-over Tris-HCl concentration from enzyme storage buffer and primers (Forward: SEQ ID NO: 21; Reverse: SEQ ID NO: 22) was 1.15 mM in the final reaction mix. Primers were designed for *Escherichia coli* 16s rRNA gene and added to the reaction at 0.5 μM final concentration each. 10 ng of *E. coli* gDNA was added to a final reaction volume of 25 μL and was initially held at 95° C. hold for 2 min, followed by 50 cycles of 95° C. for 10 sec, 55° C. for 30 sec, 68° C. for 30 sec. A change in Normalized Hue value over time (FIG. 11) indicates that this visual detection chemistry works with PCR.

Figures 12A, 12B:
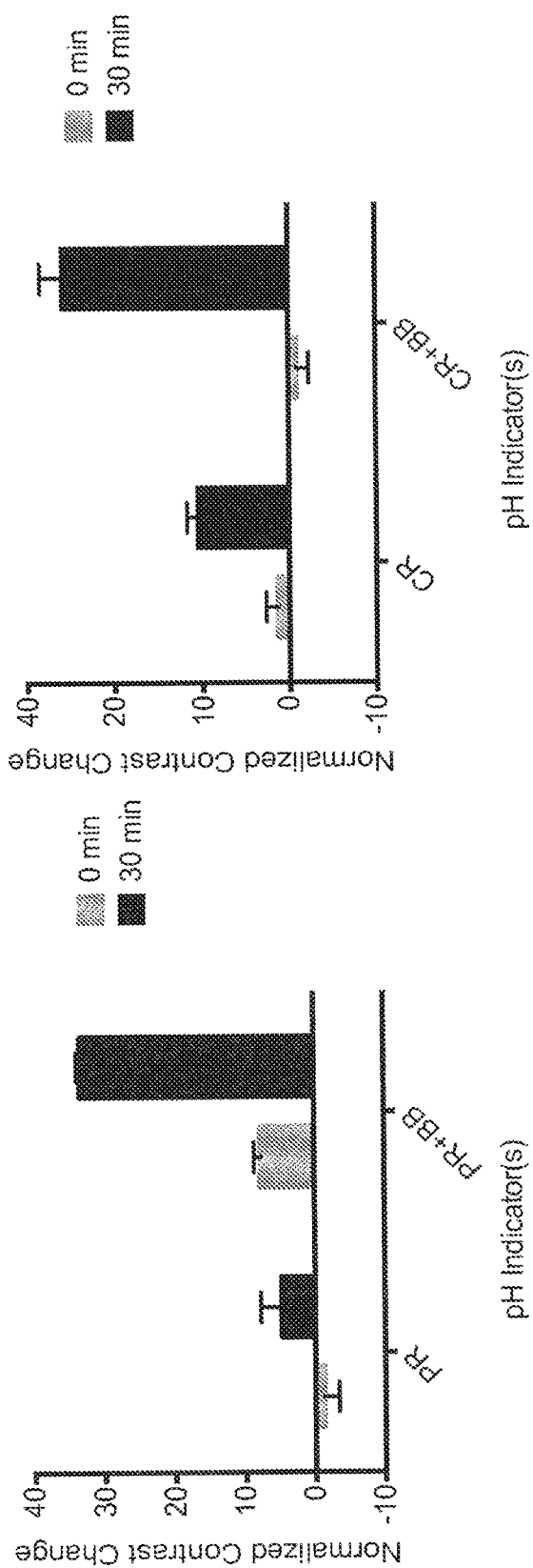
FIGS. 12A and 12B show the normalized contrast changes for amplification reactions using combinations of halochromic agents, according to an embodiment.

Example 6: Increase in Visual Detection Contrast with Combination of Halochromic Agents LAMP reactions were performed as in Example 1 with 1.3 mM final Tris buffer concentration (buffer formulated to pH 8.8), 0.8 U/μl of Bst 2.0 DNA Polymerase and 5 ng lambda DNA template. The color change contrast was evaluated for Phenol Red at 50 μM concentration and combination of Phenol Red and Bromothymol Blue at 50 μM and 160 μM concentrations respectively (FIG. 12A). The color change contrast was also evaluated for Cresol Red at 260 μM concentration and combination of Cresol Red and Bromothymol Blue at 260 μM and 160 μM concentrations respectively (FIG. 12B). The contrast values were calculated from the RGB values of images of the reaction mix using the formula: 0.299R+0.587G+0.114B. The normalized contrast change was defined as the difference between positive and negative reaction contrast values normalized to the background. The increase in the normalized contrast change with the use of the halochromic agent combination demonstrates the utility of such combinations.

Figure 13:
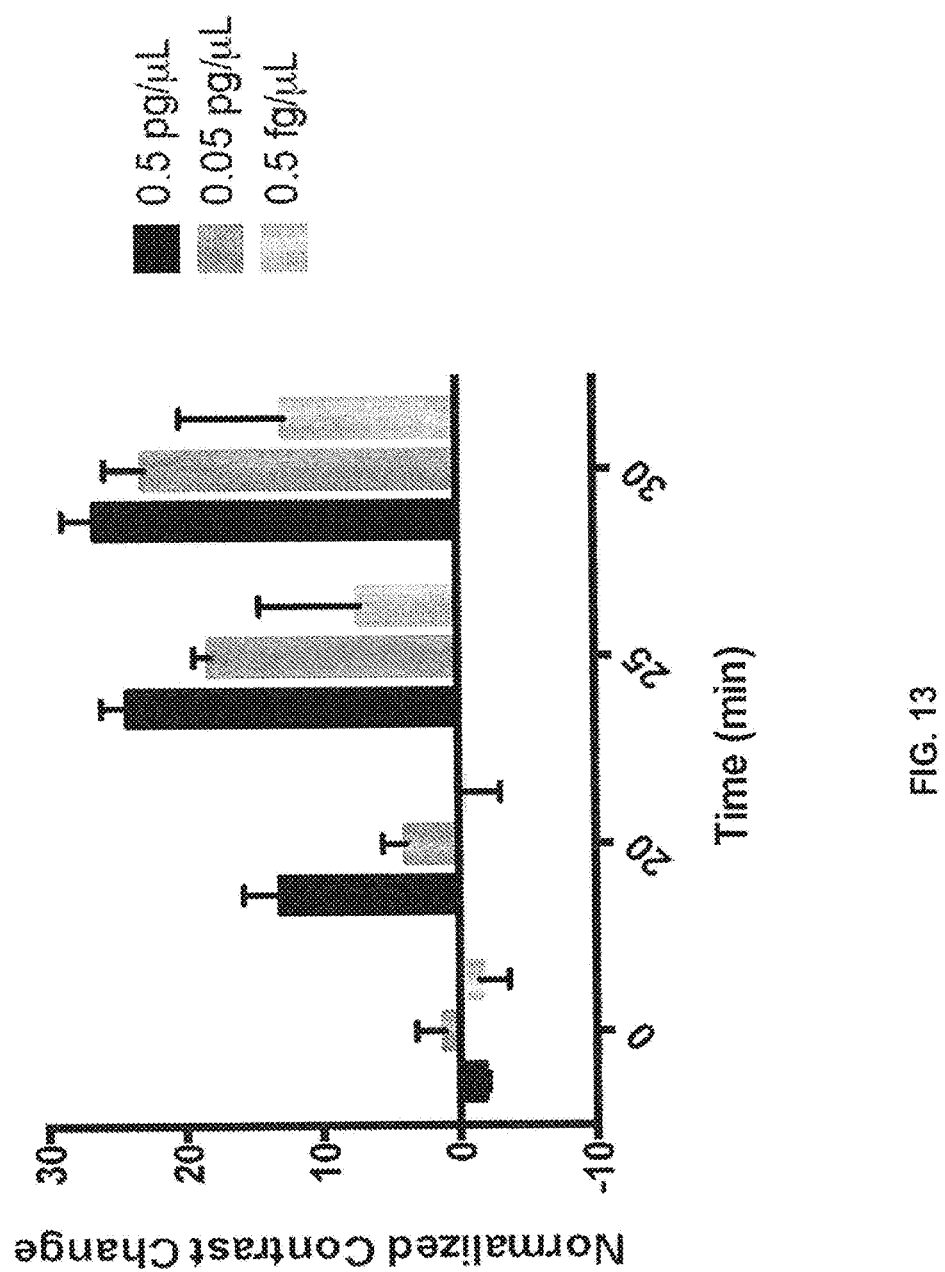
FIG. 13 shows the normalized contrast changes over time for different DNA template concentrations, according to an embodiment.

Example 7: Real-Time Color Monitoring of Amplification for Quantification Using Visual Halochromic Agents LAMP reactions were performed as in Example 1 with 1.3 mM final Tris buffer concentration (buffer formulated to pH 8.8), 0.8 U/μl of Bst 2.0 DNA Polymerase, Phenol Red and Bromothymol Blue at 50 μM and 160 μM concentrations respectively and varying lambda DNA template concentrations. Color change contrast was evaluated for lambda DNA target at 0.5 fg/μl, 0.05 pg/μl and 0.5 pg/μl final concentrations. The contrast values were calculated from the RGB values of images of the reaction mix as described in Example 5. The results (FIG. 13) indicate that the higher DNA concentrations led to a detectable change in visual contrast earlier than the lower DNA concentrations. Hence, we demonstrate the ability to distinguish between different target concentrations with the real-time color monitoring of this chemistry.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

The invention claimed is:

1. A composition of matter for colorimetric detection of an amplification reaction product in a sample, the composition of matter comprising a reaction mix comprising:
a buffer comprising one or more buffering agents, the buffer having a net buffering capacity equivalent to Tris buffer at a concentration between 1.5 mM-19 mM in a solution having a pH of 8.0;
an enzyme for catalyzing an amplification reaction; and
a colorimetric agent having a transition pH range between a starting pH of the reaction mix and an expected ending pH of the reaction mix, the expected ending pH of the reaction mix affected by the amplification reaction.

2. The composition of matter of claim 1, wherein a colorimetric change of the colorimetric agent caused by the amplification reaction is capable of being quantified at a cell path length of 50 µm.

3. The composition of matter of claim 1, wherein the reaction mix comprises at least two colorimetric agents.

4. The composition of matter of claim 1, wherein the amplification reaction is an isothermal reaction.

5. The composition of matter of claim 1, wherein the colorimetric agent is at a concentration between 50 µM-260 µM.

6. The composition of matter of claim 1, further comprising an acid or base.

7. The composition of matter of claim 1, further comprising at least one of: dNTPs, primers, and a monovalent cation.

8. The composition of matter of claim 1, wherein the enzyme is a reverse transcriptase, a DNA polymerase, a RNA polymerase, an RNase, a helicase, a recombinase, a ligase, a restriction endonuclease, a TAQ polymerase, or a single-strand binding protein.

9. The composition of matter of claim 1, wherein the colorimetric agent comprises one or more of phenol red, bromocresol purple, bromothymol blue, neutral red, naphtholphthalein, cresol red, cresolphthalein, and phenolphthalein.

10. The composition of matter of claim 1, wherein the transition pH of the colorimetric agent is between pH 5-10.

11. A composition of matter for colorimetric detection of an amplification reaction product in a sample, the composition of matter comprising a reaction mix comprising:
a buffer comprising one or more buffering agents, the buffer having a net buffering capacity equivalent to Tris buffer at a concentration between 1.5 mM-19 mM in a solution having a pH of 8.0;
an enzyme for catalyzing an amplification reaction; and
a halochromic agent.

12. The composition of matter of claim 11, wherein the halochromic agent is at a concentration between 50 µM-260 µM.

13. The composition of matter of claim 11, further comprising at least one of: dNTPs, primers, and a monovalent cation.

14. The composition of matter of claim 11, wherein the enzyme is a reverse transcriptase, a DNA polymerase, a RNA polymerase, an RNase, a helicase, a recombinase, a ligase, a restriction endonuclease, a TAQ polymerase, or a single-strand binding protein.

15. The composition of matter of claim 11, wherein the halochromic agent has a transition pH range between a starting pH of the reaction mix and an expected ending pH of the reaction mix, the expected ending pH of the reaction mix affected by the amplification reaction.

16. The composition of matter of claim 15, wherein the transition pH of the halochromic agent is between pH 5-10.

17. The composition of matter of claim 4, wherein the isothermal reaction is a strand displacement amplification, a multiple displacement amplification, a recombinase polymerase amplification, a helicase dependent amplification, a rolling circle amplification, or a loop mediated isothermal amplification.

18. The composition of matter of claim 1, further comprising an acid.

19. The composition of matter of claim 1, further comprising a base.

20. The composition of matter of claim 4, wherein the isothermal reaction is a loop mediated isothermal amplification.

21. The composition of matter of claim 20, further comprising at least one of: dNTPs, primers, and a monovalent cation.

22. The composition of matter of claim 20, wherein the transition pH of the colorimetric agent is between pH 5-10.

23. The composition of matter of claim 20, wherein the colorimetric agent is at a concentration between 50 µM-260 µM.

24. The composition of matter of claim 20, wherein the enzyme is a DNA polymerase.

25. The composition of matter of claim 20, wherein the enzyme is a RNA polymerase.

26. The composition of matter of claim 11, wherein the amplification reaction is an isothermal reaction.

27. The composition of matter of claim 26, wherein the isothermal reaction is a loop mediated isothermal amplification.

28. The composition of matter of claim 26, further comprising at least one of: dNTPs, primers, and a monovalent cation.

29. The composition of matter of claim 26, wherein the transition pH of the halochromic agent is between pH 5-10.

30. The composition of matter of claim 26, wherein the halochromic agent is at a concentration between 50 μM-260 μM.

31. The composition of matter of claim 26, wherein the enzyme is a DNA polymerase.

32. The composition of matter of claim 26, wherein the enzyme is a RNA polymerase.

33. The composition of matter of claim 26, wherein the halochromic agent is a fluorescent agent.

* * * * *

```
                         SEQUENCE LISTING

<160> NUMBER OF SEQ ID NOS: 23

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gatctgaatc cgaccaaccg                                                   20

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aacgcccacg ctctcgca                                                     18

<210> SEQ ID NO 3
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aaatccgtcc agtggttttt ttgaaaatcg ttgtatctcc g                           41

<210> SEQ ID NO 4
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
```
ccgaaaccac tggacggatt tttatttta atctaaaaca aacatc     46

<210> SEQ ID NO 5
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cgaactgttt cgggattgca ttctggaact ccaaccatcg ca     42

<210> SEQ ID NO 6
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggagcctgca taacggtttc gtcgactcaa tgctcttacc tgt     43

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gttggtcact tcgacgtatc g     21

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gctcgccgac tcttcacgat     20

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tttgcagacc tctctgcc     18

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10 ggattttta tatctgcaca     20

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tctctgattt ggtcgtattg g                                              21

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ctcctggaag atggtgatg                                                 19

<210> SEQ ID NO 13
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gttgaggtca atgaaggggt caaccagggc tgcttttaac                          40

<210> SEQ ID NO 14
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ttccacccat ggcaaattcc aggatttcca ttgatgacaa gc                       42

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggcaacaata tccactttac ca                                             22

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
accgtcaagg ctgagaac                                                  18

<210> SEQ ID NO 17
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
accgcatcga atgcatgtct cgggcaaaat gctgggatta tagatgt                    47

<210> SEQ ID NO 18
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggattccgct ccagacttct cgggcagttg gtaagtaaat ggaaga                     46

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tccttgaact ttggtctcc                                                   19

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cagttcataa aggaattgat agc                                              23

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
agcggggagg aagggagtaa agtt                                             24

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cagtatcaga tgcagttccc aggtt                                            25

```
<210> SEQ ID NO 23
<211> LENGTH: 121
<212> TYPE: DNA
<213> ORGANISM: Schistosoma mansoni

<400> SEQUENCE: 23
gatctgaatc cgaccaaccg ttctatgaaa atcgttgtat ctccgaaacc actggacgga       60
tttttatgat gtttgtttta gattatttgc gagagcgtgg gcgttaatat aaaacaagaa      120
t                                                                     121
```